United States Patent [19]

Adams et al.

[11] Patent Number: 6,025,124
[45] Date of Patent: *Feb. 15, 2000

[54] MARKER, METHOD AND AN ASSAY FOR DETECTION AND MONITORING OF LATENCY AND ACTIVATION OF HUMAN IMMUNODEFICIENCY VIRUS

[75] Inventors: Melanie Adams, San Francisco; Joseph Romeo, Palo Alto; Boris Matija Peterlin, San Francisco; Michael Paul Busch, Madera, all of Calif.

[73] Assignee: The Regents of the University of California, Oakland, Calif.

[*] Notice: This patent is subject to a terminal disclaimer.

[21] Appl. No.: 08/752,722

[22] Filed: Nov. 19, 1996

Related U.S. Application Data

[63] Continuation-in-part of application No. 08/206,384, Mar. 3, 1994, Pat. No. 5,576,176.
[51] Int. Cl.[7] .............................. C12Q 1/68; C07H 21/04; C12P 19/34
[52] U.S. Cl. .................................. 435/5; 435/6; 435/91.2; 435/91.21; 435/91.51; 536/24.32; 536/24.33; 536/24.1; 536/23.1
[58] Field of Search ..................................... 435/5, 6, 91.2, 435/91.21, 91.51; 536/24.32, 24.33, 23.1, 24.1; 935/8, 17, 18, 77, 78

[56] References Cited

PUBLICATIONS

Adams et al, Proceedings National Academy of Sciences, USA (Apr. 1994) 91:3862–3866.
Buck et al, Science (1990) 248:208–212.

*Primary Examiner*—Carla J. Myers
*Attorney, Agent, or Firm*—Hana Verny

[57] ABSTRACT

A TAR marker, method for detection and monitoring of HIV latency and activation and an assay for detection of the marker. The assay sensitively detects HIV transcription and monitors HIV transcriptional activity by detecting the presence of TAR fragments and full length transcripts, quantifying both and determining the ratio of short to long transcripts. A low ratio correlates with a latent-type transcriptional activity of HIV whereas the appearance of long transcripts signifies increased efficiency of transcriptional activity of HIV and the transition from latency to activation. The size difference between the TAR fragments appearing predominantly in latency and the full length transcripts appearing predominantly during the HIV activation is detected by RT-PCR assay that utilizes novel primers and probes. The obtained ratio is a sensitive tool in detection of HIV infection, the analysis of load of latent and active virus and monitoring the transition from the latent to active state of HIV replication.

14 Claims, 12 Drawing Sheets

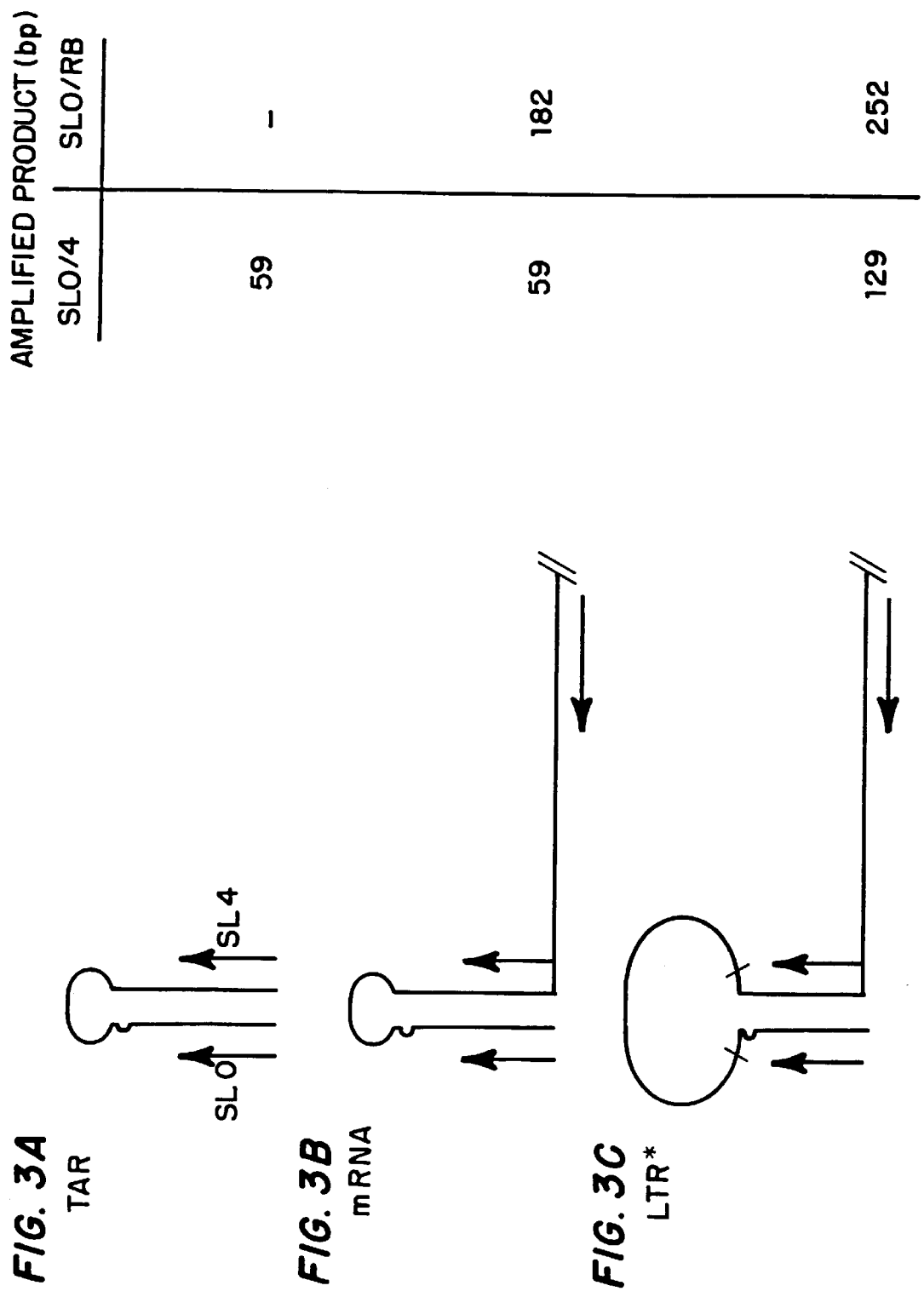

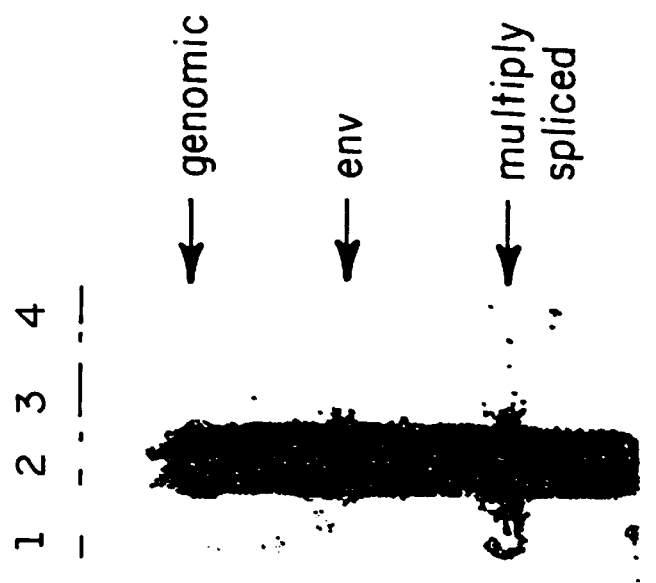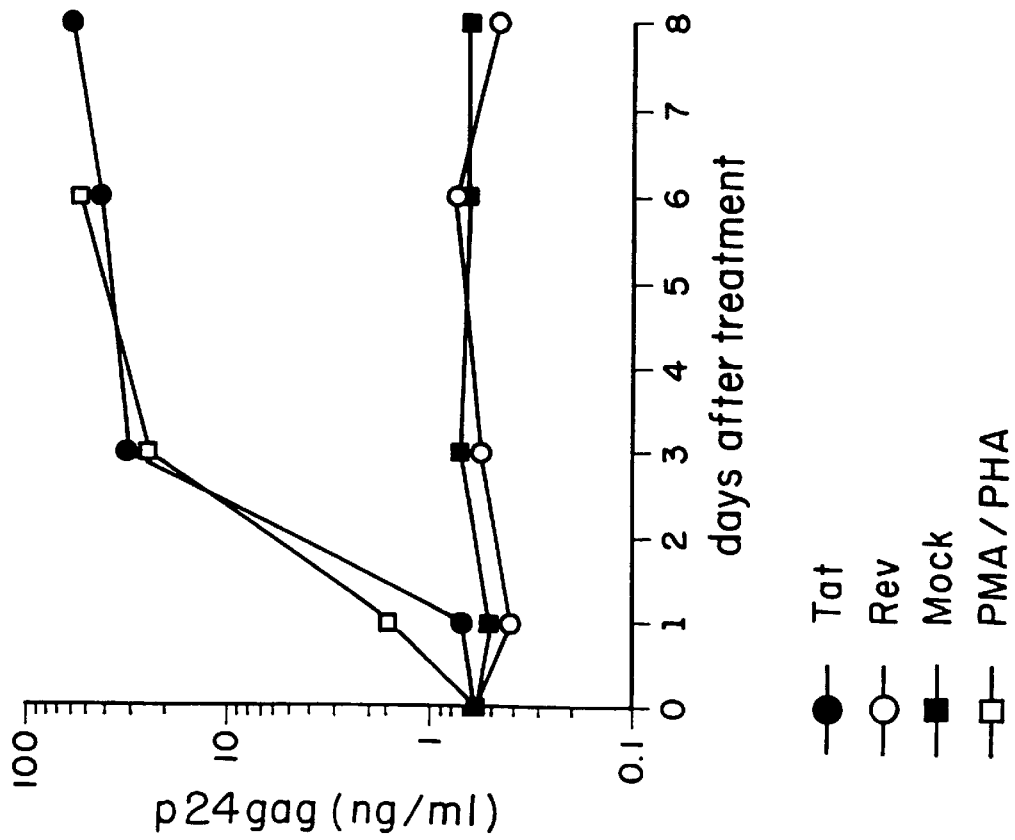

← genomic →
← env →
← multiply spliced →

PHA PMA d4 — 1:1

TAT
- d8 — 1:1
- d4 — 1:10 d0 — 1:100

LTR (RNA copy)

$10^2$
$10^3$
$10^4$

LA ↑    SA ↑

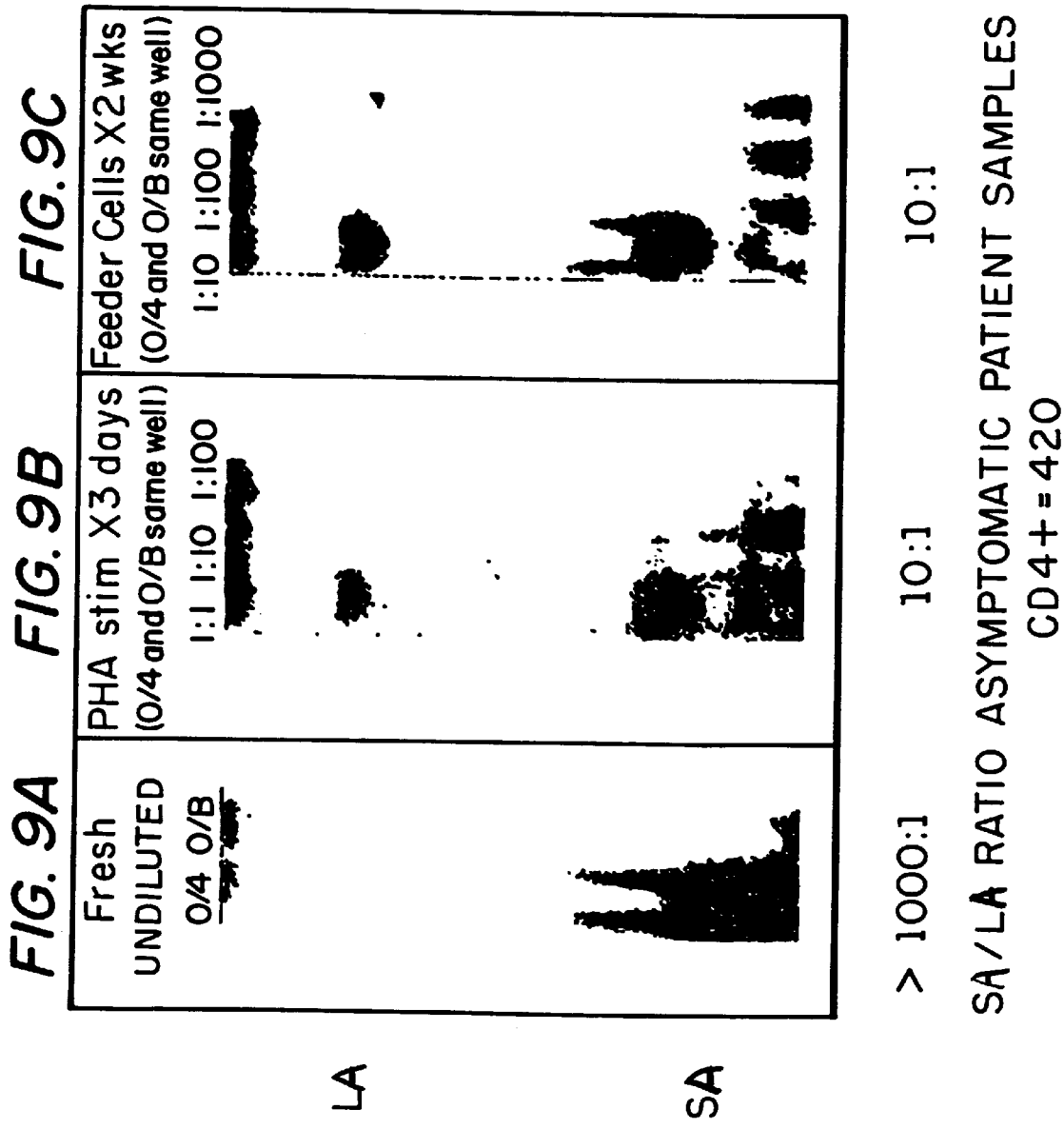

SA/LA RATIO AIDS PATIENT SAMPLE
CD4+=36

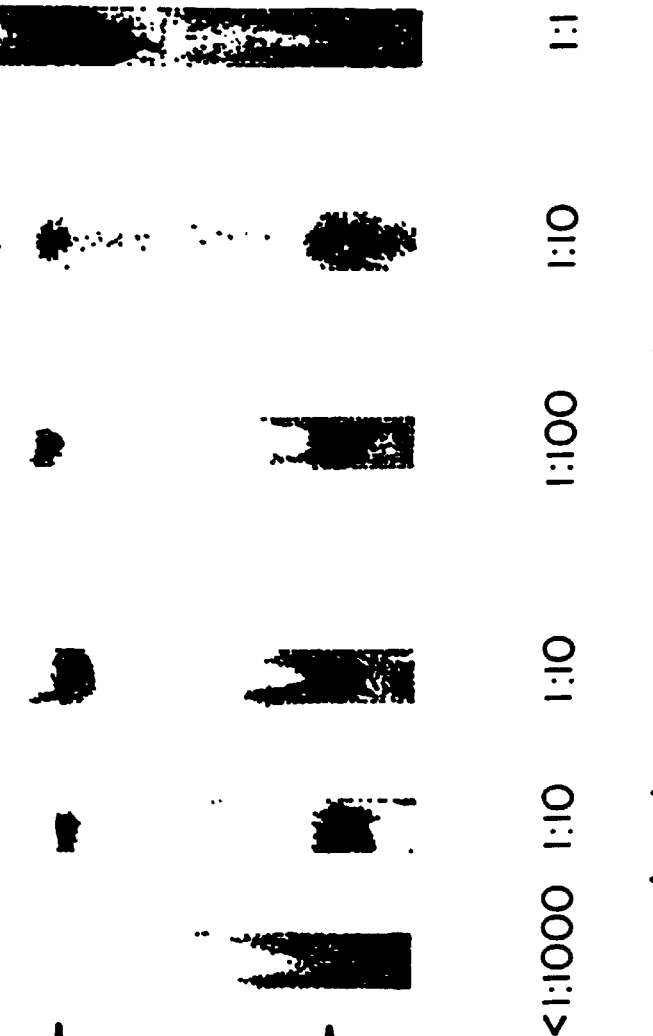

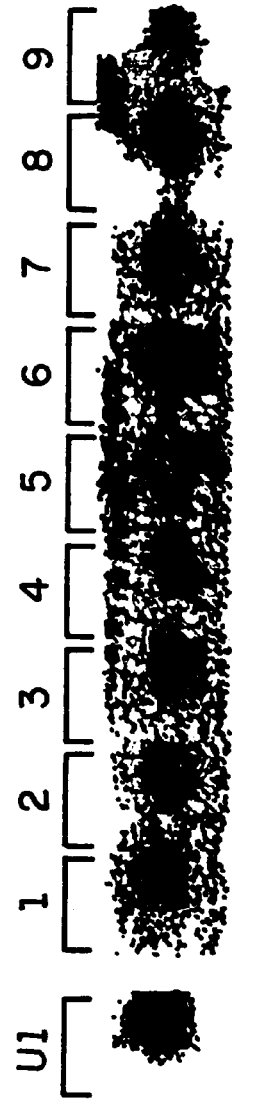
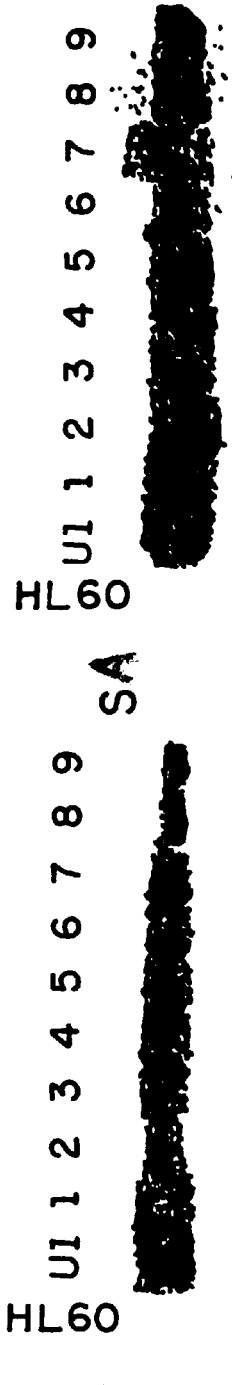
FIG.12A LT RNA
FIG.12B SA DNA
FIG.12C LA
FIG.12D

SEQUENCE LISTING (1) GENERAL INFORMATION:

(iii) NUMBER OF SEQUENCES:7

(2) INFORMATION FOR SEQ ID NO:1:

(i) SEQUENCE CHARACTERISTICS:
        (A) LENGTH:  59 base pairs (B) TYPE: nucleic acid (C) STRANDEDNESS: single (D) TOPOLOGY: linear (ii) MOLECULE TYPE: synthetic oligonucleotide (iii) SEQUENCE DESCRIPTION: SEQ ID NO: 1:

GGGTCTCTCT GGTTAGACCA GATTTGAGCC TGGGAGCTCT                              40

CTGGCTAACT AGGGAACCC                                                    59

(2) INFORMATION FOR SEQ ID NO:2:

(i) SEQUENCE CHARACTERISTICS:
        (A) LENGTH:  17 base pairs (B) TYPE: nucleic acid (C) STRANDEDNESS: single (D) TOPOLOGY: linear (ii) MOLECULE TYPE: synthetic oligonucleotide (iii) SEQUENCE DESCRIPTION: SEQ ID NO: 2:

GGGTCTCTCT GGTTAGA                                                      17

(2) INFORMATION FOR SEQ ID NO:3:

(i) SEQUENCE CHARACTERISTICS:
        (A) LENGTH:  17 base pairs (B) TYPE: nucleic acid (C) STRANDEDNESS: single (D) TOPOLOGY: linear (ii) MOLECULE TYPE: synthetic oligonucleotide (iii) SEQUENCE DESCRIPTION: SEQ ID NO: 3:

GGGTTCCCTA GTTAGCC                                                      17

(2) INFORMATION FOR SEQ ID NO:4:

(i) SEQUENCE CHARACTERISTICS:
        (A) LENGTH:  21 base pairs (B) TYPE: nucleic acid (C) STRANDEDNESS: single (D) TOPOLOGY: linear (ii) MOLECULE TYPE: synthetic oligonucleotide -continued

```
    (iii) SEQUENCE DESCRIPTION: SEQ ID NO: 4:

GGGCGCCACT GCTAGAGATT T                                              21

(2) INFORMATION FOR SEQ ID NO:5:

(i) SEQUENCE CHARACTERISTICS:
        (A) LENGTH:  29 base pairs (B) TYPE: nucleic acid (C) STRANDEDNESS: single (D) TOPOLOGY: linear (ii) MOLECULE TYPE: synthetic oligonucleotide (iii) SEQUENCE DESCRIPTION: SEQ ID NO: 5:

AGACCAGATC TGAGCCTGGG AGCTCTCTG                                      29

(2) INFORMATION FOR SEQ ID NO:6:

(i) SEQUENCE CHARACTERISTICS:
        (A) LENGTH:  30 base pairs (B) TYPE: nucleic acid (C) STRANDEDNESS: single (D) TOPOLOGY: linear (ii) MOLECULE TYPE: synthetic oligonucleotide (iii) SEQUENCE DESCRIPTION: SEQ ID NO: 6:

GTGGCGGCCG CTCTAGAACT AGTGGATCCC                                     30

(2) INFORMATION FOR SEQ ID NO:7:

(i) SEQUENCE CHARACTERISTICS:
        (A) LENGTH:  62 base pairs (B) TYPE: nucleic acid (C) STRANDEDNESS: single (D) TOPOLOGY: linear (ii) MOLECULE TYPE: synthetic oligonucleotide (iii) SEQUENCE DESCRIPTION: SEQ ID NO: 7:

CTCGAGAGAC CGATTGATCC CTTGGGTTTC CCAGAGAGAC                          40

CAATCTGGTC TAGACTCGGA CC                                             62
```

MARKER, METHOD AND AN ASSAY FOR DETECTION AND MONITORING OF LATENCY AND ACTIVATION OF HUMAN IMMUNODEFICIENCY VIRUS

This is a continuation-in-part of the patent application Ser. No.: 08/206,384, filed Mar. 3, 1994, issued as U.S. Pat. No. 5,576,176 on Nov. 19, 1996.

The invention was made with government support under Training Grant No. T32-HL-07100-16 and 17, awarded by the National Institute of Health. The United States Government may have certain rights in this invention.

BACKGROUND OF THE INVENTION

Field of Invention

This invention concerns a TAR RNA fragment marker for detection of human immunodeficiency virus (HIV) latency and activation and a method and assay for detection and monitoring of HIV latency and activation. The assay sensitively detects HIV transcription and monitors HIV transcriptional activity by detecting the presence of short non-polyadenylated TAR fragments and full length polyadenylated transcripts containing a TAR fragment as a leader sequence, and quantifying both. The method involves determining a difference between and a ratio of a level of the TAR fragment utilizing a difference between absolute levels of amplified product or a ratio of amplified products. A first amplified product reflects total viral RNA. The second amplified product reflects the full length RNA.

In particular, the invention utilizes the discovery that a unique short RNA transcript, the transactivator response element (TAR), is present in abundance in the peripheral blood mononuclear cells of (PBMC) of asymptomatic HIV subjects. The abundance of these TAR fragments make them a good marker for the presence of virus and the estimate of the total amount of TAR fragment and the ratio of total viral RNA to full-length transcripts correlates well with increased processive transcriptional activity of HIV, leading to increased replication of the virus. The size difference between the TAR fragments, appearing predominantly in latency, and the full length transcripts appearing predominantly during HIV activation, is detected by RT-PCR utilizing novel primers and probes and expressed as a ratio that equals total viral RNA to full length RNA. The ratio reflects the relative amounts of TAR fragment. The obtained ratio is a sensitive tool in detection of HIV infection, and a unique tool for determining the load of latent and active virus. The method is useful for monitoring the transition from the latent to active state of HIV replication. The assay, according to the invention, detects the presence of short TAR fragments and full length transcripts, quantifies both and determines the difference between and a ratio of short TAR fragments to full length transcripts.

BACKGROUND ART AND RELATED ART DISCLOSURES

Human immunodeficiency virus infections are serious medical, epidemiological and social problems. The infection is caused by one of several related retroviruses that become incorporated into host cell DNA and result in a wide range of clinical presentations varying from asymptomatic carrier states to severely debilitating and fatal disorders including opportunistic infections, malignancies, and neurologic dysfunctions.

The human immunodeficiency virus (HIV) is a human lentivirus capable of both establishing long-term latency and rapidly destroying its host. Its replicative versatility is determined in part by the surprisingly complex array of mechanisms by which the virus regulates its gene expression. While much research has been directed towards the elucidation of these mechanisms in vitro, little is known about viral transcriptional activity in vivo. Of particular interest is how viral gene expression is regulated during the long delay between the initial infection and the eventual devastation of the immune system. This remains one of the most enigmatic features of HIV disease. The elucidation of the mechanisms underlying the pathogenesis of human immunodeficiency virus, therefore, remains one of the foremost challenges facing the medical research community.

Evidence is accumulating that blocked viral replication may contribute to the relative latency of early infection. Unfortunately, studies of viral transcription patterns in primary infected cells are limited by the variable sensitivity of the assays employed. Studies described in *Science*, 245:305 (1989) and in *N. Engl. J. Med.*, 326: 1385 (1992) employing in situ polymerase chain reaction (PCR) for the detection of proviral DNA, report that numerous peripheral blood mononuclear cells (PBMC) contain integrated provirus: up to 1 in 10–100 CD4+ cells. However, RNA analysis by in situ hybridization revealed that, even in AIDS patients, only 1 in 1,000 infected cells produce detectable RNA. It is not known whether these HIV DNA-positive, RNA-negative cells contain transcriptionally silent provirus or if undetected RNA is present.

Recently, the patterns of spliced and unspliced HIV-1 mRNA expression in a population of primary infected cells have been examined with a quantitative reverse transcription-PCR technique described in *PNAS (USA)*, 89: 10663 (1992). This method reveals that median levels of singly and doubly spliced mRNA coding for viral envelope and regulatory proteins, respectively, are higher than median levels of unspliced mRNA coding for structural and replicative proteins in asymptomatic subjects. In ARC/AIDS subjects the levels of spliced mRNA decrease and levels of unspliced mRNA increase, possibly reflecting a shift from a "blocked early-stage latency". The authors speculate that low levels of viral transcription result in low levels of the virally-encoded protein Rev, required for the switch in splicing patterns. However, the low levels of viral transcription may be determined by limitation of other protein Tat.

There are multiple cellular factors involved in the initiation of HIV transcription. However, there is good reason to believe that it is the virally encoded transactivating protein Tat that plays the pivotal role in the activation of viral gene expression. Tat has been described in *EMBO J.*, 9:4417 (1990) to be a potent transactivator of transcription and a necessary component of HIV replication. The interaction of Tat with the transcription complex is unique among known eukaryotic transcriptional transactivators in two respects. First, while other transactivators bind DNA, Tat binds an RNA structure, the transactivator response element (TAR), which is at the 5'-end of all HIV nascent transcripts (*Cell*, 62: 769 (1990)). Second, although the means by which Tat activates transcription remains controversial, it has been reported in *Nature*, 330:489 (1987), *Cell*, 59: 229 (1989) and *Cell*, 63: 655 (1990), that one of the key functions of Tat is its effect on transcriptional elongation. In its absence, transcription is initiated but not completed, leading to the accumulation of the TAR fragment which a is stable stem-loop structure. Abundant TAR fragments are the signature of the absence of Tat, which in turn is the signature of a latent virus.

The understanding of HIV disease is incomplete and it is unknown how long the asymptomatic stage is maintained as well as what triggers the turning point between asymptomatic and fully symptomatic disease. Since the treatment and prevention of various symptoms and complications accompanying and connected with AIDS depends on the assessment of latently infected cells and detection of the transition from the latent to acute state of HIV replication, it would therefore be extremely important to provide the means to detect such transition and/or monitor the actual HIV transcriptional activity.

It is therefore a primary object of this invention to provide a marker for latency and an assay for early detection of HIV and HIV activation from inactive to active stage.

SUMMARY

One aspect of the current invention is identification of a TAR marker present in infected peripheral blood mononuclear cells from HIV positive but asymptomatic patients, which marker is suitable for early detection of the HIV infection, for assessing the load of latently infected cells, and for detection and monitoring of the degree of HIV transcription activation.

Another aspect of the current invention is an HIV marker which is a unique short RNA transcript fragment encoding the trans-activator response (TAR) element present in abundance in the PBMC in large number of asymptomatic HIV patients.

Another aspect of this invention is a method for analysis of viral latency and activation wherein an absolute value, a difference between and a ratio of TAR fragments and full length transcripts are calculated.

Yet another aspect of this invention is an assay for detection of a ratio of short TAR fragments and long full length viral mRNA.

Another aspect of the current invention is a reverse transcription polymerase chain reaction or branch chain DNA assay for detection of the short RNA transcript fragments encoding the transactivator response element.

Still another aspect of the current invention is an assay for detection and quantitation of TAR fragments and full length transcripts of viral mRNA and for determination of their absolute amounts, difference and a ratio.

Still another aspect of the current invention are the primers and probes useful for detection, amplification and determination of a ratio of short and long amplicons that reflects the viral short and long transcripts used in an assay for detection of a degree of the HIV transcription activation.

Still yet another aspect of the current invention is a method for determination and monitoring of progression of HIV activation.

DEFINITIONS

As used herein:

"LTR" means the Long Terminal Repeat, a 713 base pair DNA sequence repeated at the 5' and 3' ends of the HIV genome, which consists of the enhancer and promoter regions for gene expression (U3 region), and the RNA start site, and the untranslated RNA sequences (RU5) such as the genomic repeat and polyadenylation sites.

"Tat" means the virally encoded trans-activating protein which functions as an elongation factor. Tat is essential for viral replication as the key viral element for increasing HIV gene expression.

"TAR" means the Trans-Activating Response element which is the target for Tat binding. The TAR region is the first 59–61 nt of RNA, the leader sequence positioned immediately 3' of the transcription start site. It forms a stem-loop structure.

"TAR fragment", "short TAR transcript" or "promoter-proximal transcript" are used interchangeably and mean the non-polyadenylated RNA transcript. In the absence of Tat protein, TAR fragments are found in the nucleus and cytoplasm as stable RNA stem-loops.

"Full length viral mRNA" or "full length transcript" or "long transcript" or "promoter-distal RNA" are used interchangeably and mean polyadenylated viral mRNA. The TAR sequence forms the leader sequence of the full length viral mRNA. In the presence of Tat, viral RNA is elongated beyond the TAR leader sequence and is polyadenylated into full length viral mRNA. Full length viral mRNA includes both spliced and unspliced mRNA.

"Short amplicon" or "(SA)" means the short amplified product generated from PCR utilizing primer pairs which encompass the TAR region. The amount of short amplicon is directly proportional to the total amount of viral RNA present in the sample which includes the non-polyadenylated TAR fragments and all polyadenylated viral RNA species (polyadenylated transcripts contain the TAR leader sequence and are amplified by this primer pair).

"Long amplicon" "(LA)" means an amplified product generated from PCR utilizing primer pairs which encompass the RU5 region of the viral LTR. The amount of long amplicons is directly proportional to the amount of full length mRNA and genomic RNA present in the sample.

"Total RNA transcripts" means short TAR transcripts plus full length transcripts containing the TAR leader sequence. The amount of total transcripts is directly proportional to the amount of short amplicon.

"Processive transcription" means efficient elongation of transcripts leading to high levels of polyadenylated mRNA.

"Nonprocessive transcription" means initiation with inefficient elongation (transcription complexes pause and drop of the DNA) leading to an abundance of short, non-polyadenylated RNA and only rarely in elongated full length mRNAs.

"Processivity ratio" or "(SA/LA)" means the ratio of amplified products which reflects the ratio of total transcripts to polyadenylated transcripts. The processivity ratio reflects the type of transcription (processive/nonprocessive) that predominates in the sample. A processivity ratio of 1 indicates a totally processive mode of transcription and values >1 indicate the degree of nonprocessive transcription.

"Difference" means the value obtained when the absolute value of the long amplicons is subtracted from the absolute value of short amplicons.

"Latency" means a concept describing 1) an asymptomatic clinical condition, 2) the state of viral activity within a population of cells, or 3) the down-regulation or absence of gene expression within an infected cell.

"AIDS" means acquired immunodeficiency syndrome which is a systemic immunodeficiency characterized by decreasing CD4+T lymphocytes and increasing susceptibility to opportunistic infection.

BRIEF DESCRIPTION OF DRAWINGS

FIGS. 3A–3C illustrates primer placement and the size of RT-PCR amplified product TAR (FIG. 3A), mRNA (FIG.

3B) and internal control (LTR*) (FIG. 3C) with specifically designed probes SL0, SL4, U5.1 primer, LOOP probe and LTR* LOOP probe.

Figures 4A, 4B, 4C:
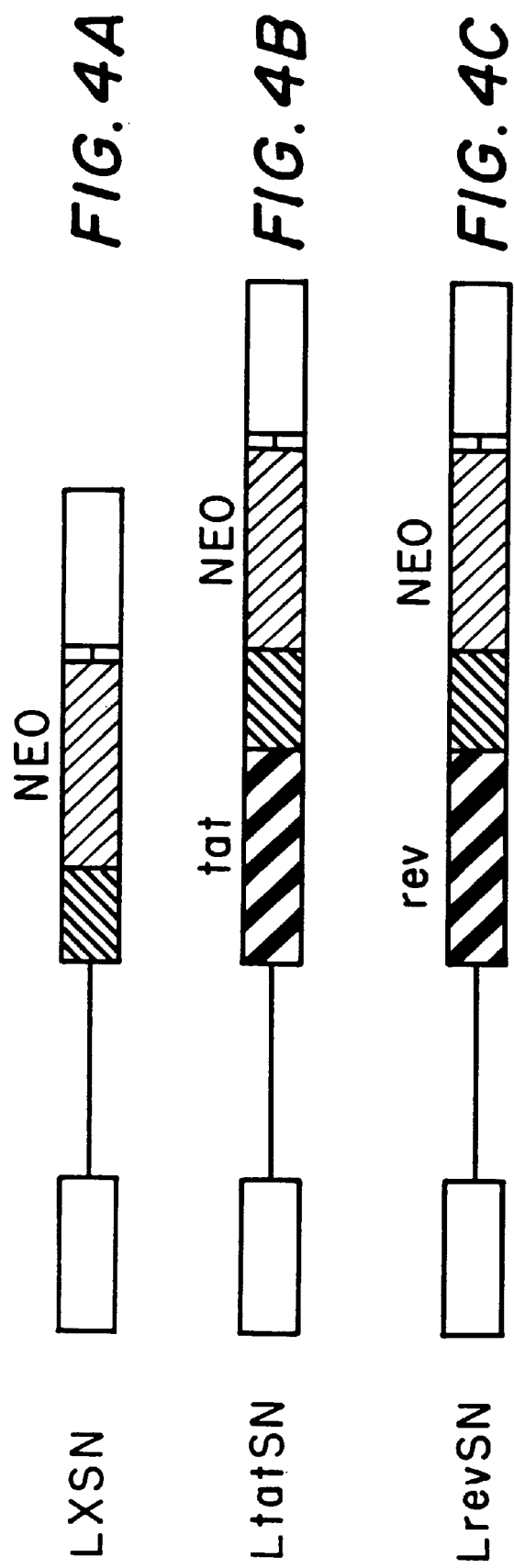

FIGS. 4A–4C illustrates the structure of retroviral vectors used in the analysis of Tat protein in latency: important background for development of this invention.

FIG. 5 illustrates the effect of constitutively produced Tat and Rev protein on the expression of viral p24 proteins in transduced U1 cells in the culture supernatant (FIG. 5A) and northern blot (FIG. 5B).

Figure 6:
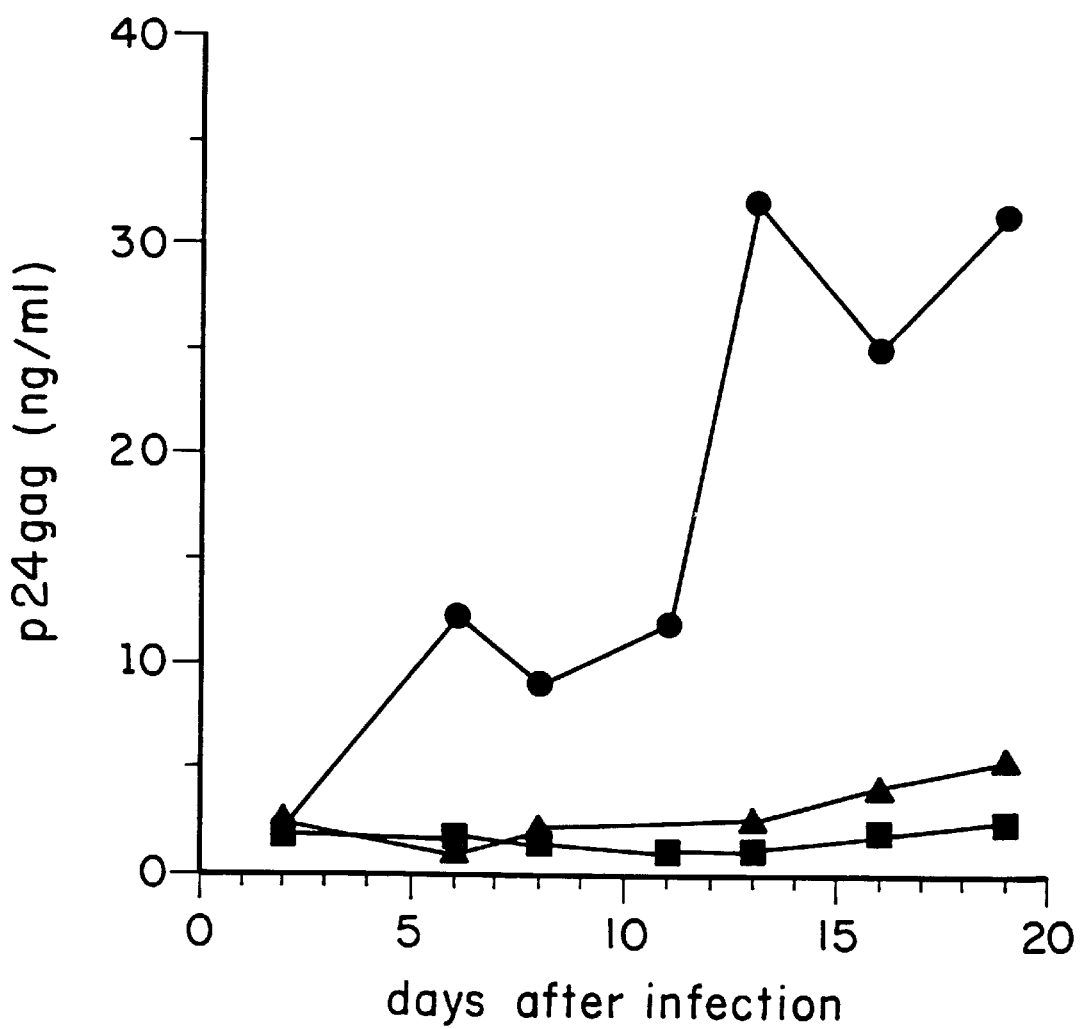

FIG. 6 illustrates viral spread in U937 cells that is accelerated by constitutive expression of Tat but not Rev.

Figure 7A:
Figure 7B:

FIG. 7 is a Northern blot showing Tat induced major classes of viral mRNAs in U1 cells; unstimulated U1 cells (FIG. 7A) and U1 cells stimulated with PMA/PHA (FIG. 7B).

FIG. 8 illustrates HIV-1 transcription in resting, activated and Tat infected U1 cells (FIG. 8A) and detection of transcripts initiated from the HIV-1 LTR in U1 cells by RT-PCR (FIG. 8B).

FIG. 9 depicts an asymptomatic subject with a high ratio of short amplicons (SA) to long amplicons (LA). Following PMA/PHA stimulation, long amplicons appear and the ratio drops. FIG. 9A shows SA/LA ratio in fresh undiluted PBCM. FIG. 9B shows SA/LA ratio in PHA stimulated PBCM. FIG. 9C shows SA/LA ratio in feeder cells.

Figure 10:
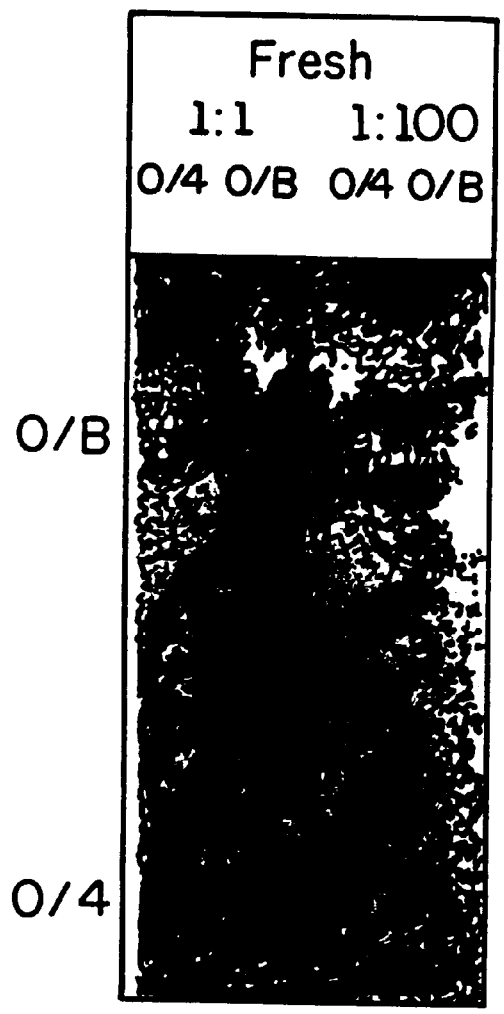

FIG. 10 illustrates a low ratio of short to long amplicons demonstrated in the PBMC of an AIDS patient.

FIG. 11 shows analysis of HIV-1 transcripts in PBMC of HIV infected individuals with CD4 counts <500 (2 asymptomatic (FIGS. 11A and 11B) and 2 AIDS (FIGS. 11C and 11D)).

FIG. 12 shows analysis of HIV-1 transcripts in PBMC of infected individuals with CD4 counts >500. No LT are detectable while ST are abundant. FIG. 12, panel A, shows long amplicons RNA; panel B shows short amplicons RNA; panel C shows amplified regions of viral DNA that corresponds to long transcripts. Panel D shows amplified regions of viral DNA that corresponds to short transcripts.

DETAILED DESCRIPTION OF THE INVENTION

This invention concerns the discovery that peripheral blood mononuclear cells from asymptomatic HIV positive subjects contain a large number of the unique TAR fragments. On the other hand, full length transcripts of mRNA were found to be present in the fully symptomatic AIDS patients.

In vitro analysis of HIV-1 transcription has shown that, in the absence of Tat, transcription initiates but is nonprocessive, leading to the synthesis of the first 59 nt of the nascent transcript consisting of the stem-loop transactivator response (TAR) element of HIV.

Surprisingly, we found that a large number of these unique short RNA transcript fragments are detectable in HIV-1 infected peripheral blood mononuclear cells (PBMC), indicating that in a large percentage of infected PBMC, the Tat protein is inhibited or absent, and the virus is latent. In HIV positive but asymptomatic subjects, there is an abundance of TAR fragments, in many cases there is a complete absence of full-length transcripts. In HIV positive subjects in acute symptomatic phase, the number of these TAR fragments decreases and full-length transcripts appear. Therefore, the ratio of the TAR fragments to all other viral mRNA is high in asymptomatic HIV phase and decreases as the disease progresses. The change in the ratio of short to long transcripts seems to be one of the earliest events of viral activation. Detection of the change in this ratio can be advantageously utilized to assess the state of HIV activation in patients. The ratio provides a tool for quantifying the load of latent virus and early detection of HIV activation which signals the progress of HIV infection from inactive to full blown HIV replication. Such early detection would provide timely information to a physician to initiate appropriate treatment at early stage as well as a sensitive monitor for drug therapy.

In the absence of Tat, there is an accumulation of TAR fragments and the presence of Tat correlates with increased expression of promoter-distal full length transcripts. The large number promoter-proximal TAR fragments correlate with a latent inactive and asymptomatic HIV infection while the presence of promoter-distal full length transcripts correlates with activation of HIV replication and disease progression. The short promoter-proximal transcripts can be amplified and their level can be detected and used as a marker for detection of HIV and estimates of the amount of latently infected cells. The ratio of short to long transcripts can be advantageously used as a method for monitoring latency and activation and as an assay for detection of the transition from inactive asymptomatic disease to activated fully symptomatic HIV disease.

The invention, therefore, concerns in one aspect a discovery of a new marker of latency of HIV replication in human cells, in a second aspect a method for detection of this marker and the transition from latency to activation and in a third aspect an assay for the marker and degree and type of HIV transcription.

I. A Marker for Detection of HIV Latency

The marker for the detection of latent stage of HIV infection is the TAR fragment which has typically 59 base pairs and in a predominant number of subjects it has the sequence '5 GGGTCTCTCTGGTTAGACCA-
GATTTGAGCCTGGGAGCTCTCTG-
GCTAACTAGGGAACCC '3 (SEQ ID No: 1).

However, there are variations in this sequence which are individual to each subject and therefore the "TAR fragment" is intended to encompass all variations, mutations, additions, and deletions of TAR fragment sequence which, therefore, is not limited solely to sequence SEQ ID NO: 1.

TAR fragment, seen as SEQ ID No: 1, is detected with a set of primers identified as primer 1 and 2 or as SL0 and SL4. The other TAR fragments containing variant sequences are detected with complementary DNA primers to said variant sequences. The TAR fragment which appears during Tat independent nonprocessive HIV transcription and is present in all HIV-positive individuals and in abundance in asymptomatic HIV positive patients. Asymptomatic stage of HIV infection is characterized by very low processive transcriptional activity due to the absence or inhibition of the protein Tat and is identified by low amounts of full-length transcripts.

It has now been discovered in studies performed in support of this invention that the Tat protein is directly involved in up-regulating processive transcriptional activity of the HIV and in triggering the transition from viral latency to activation.

II. A Method for Detection of HIV Latency and Activation

The method according to this invention for detection of the degree of HIV latency and activation utilizes determination of the relative amount of TAR fragments to full length viral mRNA TAR fragments containing transcripts. The difference between the absolute amount of total RNA and full length RNA also reflects the degree of HIV latency and activation. When the amount of short transcripts to long transcripts is larger than 1000:1 then the subject is HIV positive and has a high load of latent virus. The lower the relative amount, the higher is the degree of HIV transcriptional activation, indicating the HIV positive subject is progressing from the asymptomatic stage to the fully symptomatic AIDS state. For example, the relative amount of 10:1 signifies the activation of processive transcription and increase in full length transcripts and transition from latent to active HIV replication. The relative amount of 1:1 evidences the presence of full-length transcripts only and fully active virus. This leads to symptomatic AIDS.

A method for detection of the latent stage of the HIV infection is based on findings that 1) the PBMC of asymptomatic HIV positive subjects contain a large number of the TAR fragments and only a small number of full length transcripts; 2) the PBHC of symptomatic AIDS patients confirm a smaller number of the TAR fragments and a larger number of full length transcripts; 3) during the transition from inactive asymptomatic state of HIV infection to fully symptomatic stage there is a change in the proportion of these short and long transcripts during the progression from the inactive HIV transcription observed in asymptomatic subjects to the active HIV transcription observed in symptomatic AIDS subjects; and 4) the proportion of short transcripts to long transcripts is indicative of the activity of the Tat protein and therefore of the level of HIV transcription and the stage of disease progression.

The method is useful for monitoring the state of the HIV infection and detection of the transition from the inactive latent state to the active replicative state leading to or resulting in AIDS. In practice, the method is used to monitor the blood of HIV positive individuals and to determine the level of activity of the virus infecting that individual. The level of activity is used to indicate to a physician when therapy should be initiated, changed or increased.

III. An Assay for Detection of Latency and HIV Activation

An assay for quantitative detection of a proportion of the TAR fragments to full length transcripts in the blood samples from HIV infected subjects comprises isolation of PBMC from the whole blood samples, extraction of RNA, digestion with DNase, 4 or 10-fold serial dilutions of RNA, synthesis of cDNA by reverse transcription, amplification of the TAR region and the RU5 region (RU5 representing all viral mRNA as it is present as the untranslated leader sequences) of the cDNA with the polymerase chain reaction technique, hybridization with a $^{32}$P-labeled probe directed to the TAR and RU5 amplified products, and quantitation by polyacrylamide gel electrophoresis and autoradiography. The result of the assay is expressed as a "processivity ratio" (SA/LA) of short amplicons (SA) to long amplicons (LA) based on the last dilution at which signal is still detectable. A standard curve is generated using dilutions of the control LTR* RNA.

IV. Primers and Probes for Use in the Assay for Latency and HIV Activation

Figure 2:
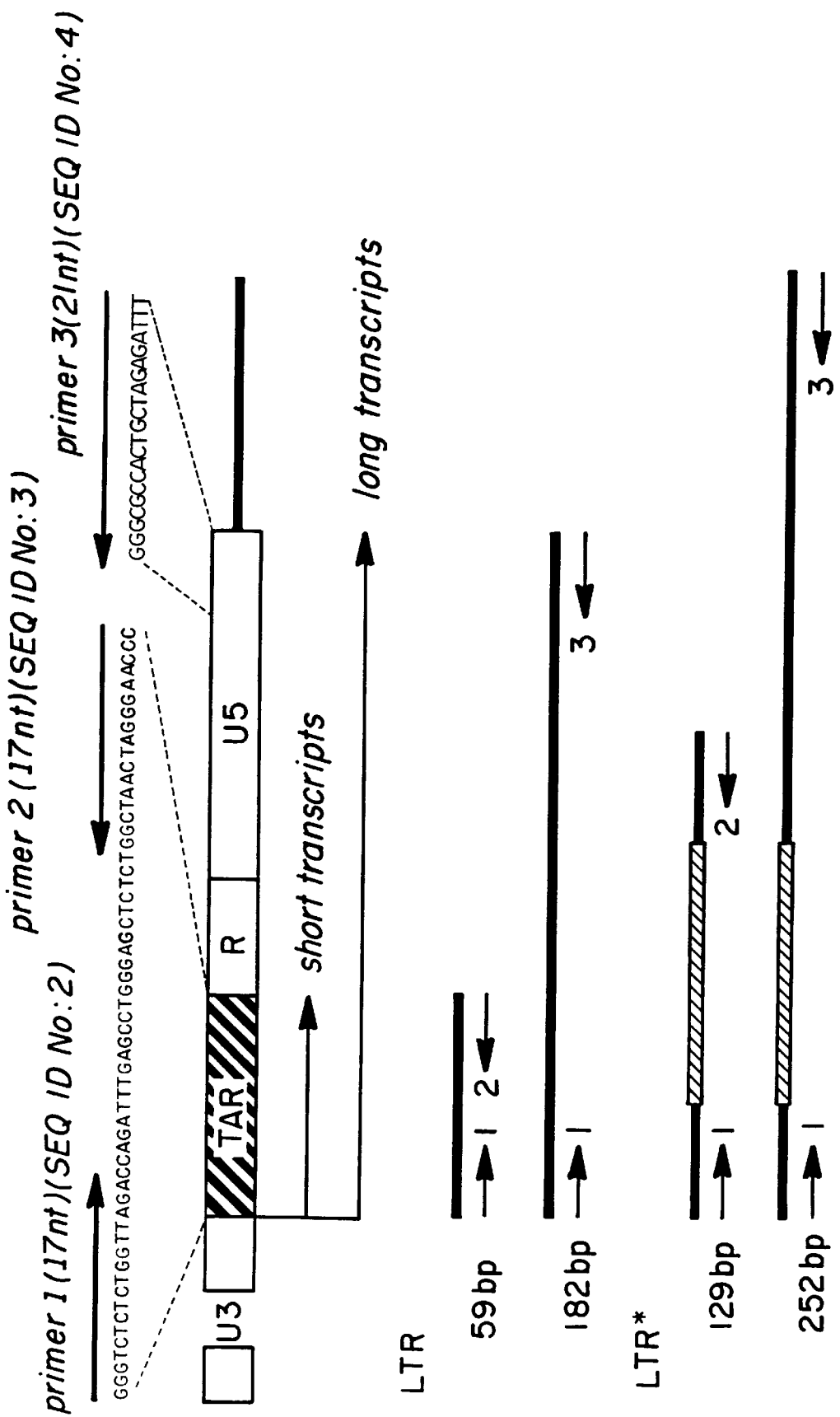
FIG. 2 is a diagrammatic representation of the HIV long terminal repeat with primers sequences used to amplify the TAR and RU5 regions.

To detect the TAR fragments identified by SEQ ID No: 1 and TAR containing full length transcripts, DNA primers were prepared as seen in FIG. 2.

Primer 1(SL0) has the following sequence (17 nt)

5' GGGTCTCTCTGGTTAGA'3 (SEQ ID No: 2);

Primer 2 (SL4) has the following sequence (17 nt)

5' GGGTTCCCTAGTTAGCC '3 (SEQ ID No: 3);

Primer 3 (U5.1) has the following sequence (21 nt)

5' GGGCGCCACTGCTAGAGATT '3 (SEQ ID No: 4);

Probe 1 (TAR loop probe) has the sequence (29 nt)

5' AGACCAGATCTGAGCCTGGGAGCTCTCTG '3 (SEQ ID No: 5);

Probe 2 (LTR* LOOP PROBE) has the following sequence (30 nt)]

5' GTGGCGGCCGCTCTAGAACTAGTGGATCCC '3 (SEQ ID No: 6).

The invention concerns discovery that latently infected cells contain high levels of TAR fragments. The abundance of these transcripts serves as a basis for the detection of HIV-infected cells by direct DNA hybridization techniques. However the small size of TAR presents technical problems when using conventional DNA probes. Cells must undergo permeabilization procedures to allow entry of the DNA probe since the probe is too large to traverse the cell membrane: probe that is hybridized to TAR may be too small to be retained within the cell membrane following the permeabilization procedures required to allow entry of the probe. This problem may be circumvented by use of a complementary probe that is permuted for the TAR sequences. Permutation of the TAR sequences in such a way that the 5' and 3' sequences are exchanged creates a hybridization probe that can mediate the concatamerization of the TAR monomers into high molecular weight polymers that will be retained within the permeabilized cell membrane. The sequence for this probe, to be used with in situ hybridization useful for slide-based or flow cytometric detection systems, is also listed below and identified as "TAR-linking" probe.

Probe 3 (TAR-linking probe) has the following sequence (62 nt)

5' CTCGAGAGACCGATTGATCCCT-
TGGGTTTCCCAGAGAGACCAATCTG-
GTCTAGACTCGGACC 3'(SEQ ID No: 7)

V. Detailed Description of Figures

HIV has been observed to be able to establish latent infection in which infected cells demonstrate extremely low levels of gene expression and viral replication. Tat is known to be an essential gene for viral replication and it has been shown to be the key viral element for up-regulating, that is increasing HIV gene transcription. Cellular control of Tat levels or function may play a part in the establishment and maintenance of latent infection. Tat binds to the initial sequence of the viral RNA, the TAR element, where it interacts with a variety of cellular proteins that mediate transcription.

Tat functions as a processivity factor, stabilizing the RNA polymerase complex as it continues transcription beyond the initial TAR region of the transcript. It has been now discovered in vitro and in cell lines infected with Tat-defective mutants of HIV, that there is an accumulation of the TAR fragments which are thought to be the primary or processed product of abortive initiation events. With the addition of Tat protein, transcription is not aborted and the TAR containing transcripts are elongated into full length transcripts of viral mRNA species.

Figure 1:
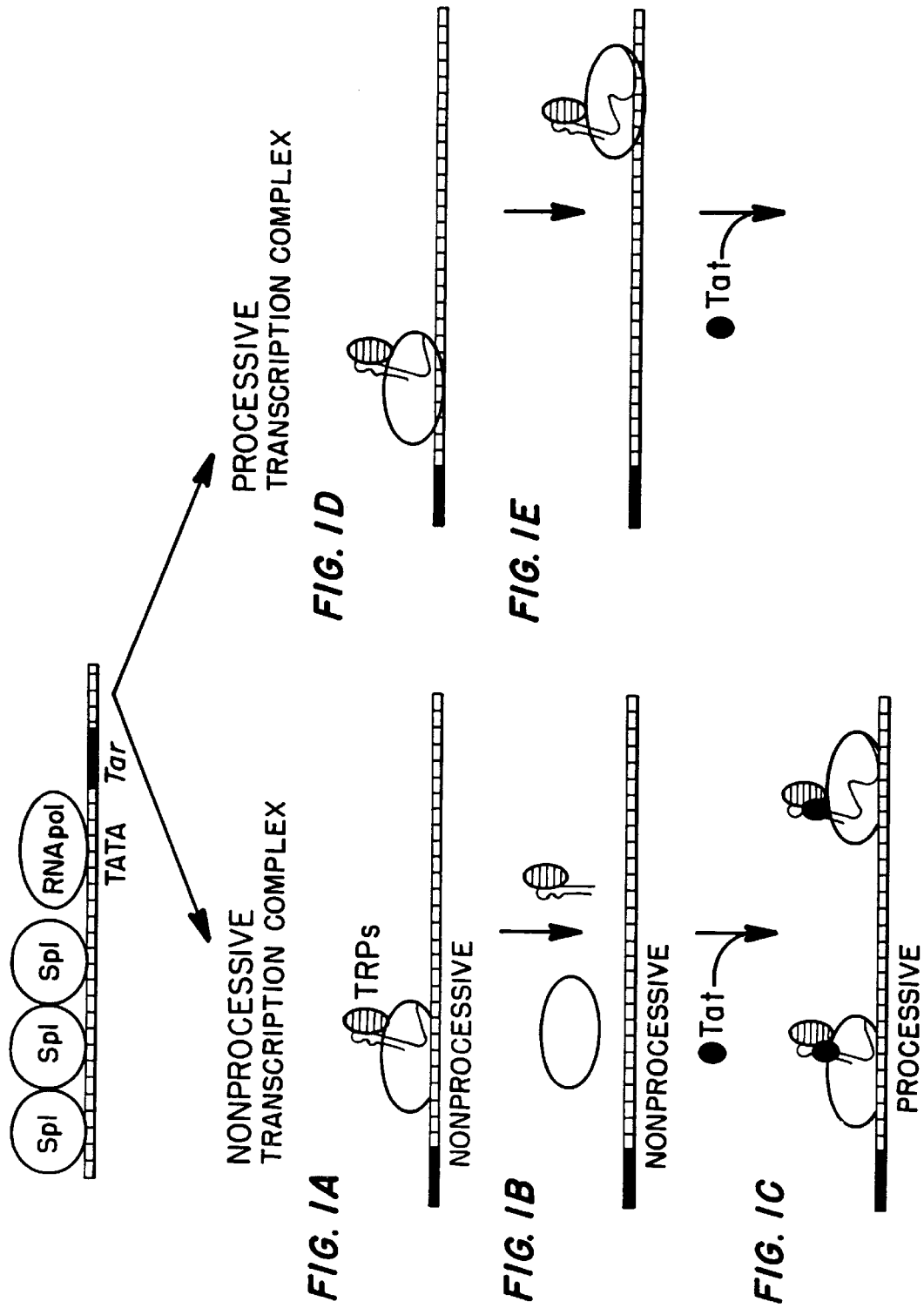
FIGS. 1A–1E is a model for HIV transcription.

This HIV transcription model is illustrated in FIG. 1. Transcription of HIV gene is either processive transcription, that is an active transcription, or non-processive which is an abortive transcription. Tat protein is a potent transactivator of the transcription complex. Tat protein is unique in that it binds to TAR stem-loop of viral mRNA. TAR stem-loop is at the 5'-end of all HIV nascent transcripts. The TAR stem-loop contains binding site for Tat protein. The main function of the Tat protein is to effect HIV transcriptional elongation. In the process of HIV transcriptional elongation, Tat binds to the TAR element where it interacts with a variety of cellular RNA-binding proteins (TRPs) that mediate transcription. These proteins, seen in FIG. 1, may complex with TAR throughout the transcription process.

Typically, transcriptional complexes initiate at the promoter region as seen in FIG. 1. When Tat is not present, the transcriptional complexes are predominantly non-processive (FIGS. 1-A and B) although some may be processive (FIGS. 1-D and E). These non-processive transcription complexes release prematurely leading to attenuated transcripts which are digested by ribonuclease to the stable TAR-stem loop structure (FIG. 1-B). This stage corresponds to and predominates in latent HIV infections. When the Tat protein becomes available, it attaches to the binding site on the TAR stem-loop and stabilizes non-processive transcription to processive transcription (FIG. 1-C) observed in active HIV replication.

In FIG. 1, a non-processive transcription complex (FIG. 1-A) releases and the prematurely attenuated RNA is digested by ribonuclease to the stable TAR stem-loop structure (FIG. 1-B). When the Tat protein becomes available or added (FIG. 1-C), transcripts are not released and are elongated full-length viral mRNA. When transcription is fully processive, TAR stem-loops are not released (FIGS. 1-C, D and E) and transcription proceeds without interruption (FIGS. 1-C and 1-E). Tat does not change the ability of an already processive transcription complex to elongate (FIGS. 1-C, D and E). Correlation is seen between the presence of an abundance of these TAR fragments and a paucity of full length transcripts and the asymptomatic disease. The appearance of elongated mRNA transcripts is seen in fully symptomatic HIV infections. These observations form the basis for the method and assay of this invention.

In the HIV replication model as diagrammed in FIG. 1, the HIV long terminal repeat (LTR) promoter directs the assembly of transcription complexes that initiate RNA synthesis but are incapable of efficient elongation in the absence of Tat, a process termed non-processive transcription. The RNA produced by these complexes consists predominantly of abortive non-polyadenylated transcripts that are released and degraded to the 5' stem-loop structure TAR (FIG. 1-B). These TAR RNA fragments are the signature of deficient Tat function. Processive transcription (FIG. 1-C) and (FIG. 1-D), with efficient elongation, predominates in the presence of Tat (FIG. 1-C). Such a system allows HIV gene expression to remain transcriptionally poised, yet silent, until cellular activation signals trigger the increase in Tat levels and the transition to fully effective viral transcription.

FIG. 2 is a schematic representation of the primers synthesized and used for the detection of transcripts initiated from the HIV-1 long terminal repeat (LTR) by reverse transcriptase polymerase chain reaction (RT-PCR).

A schematic representation of the HIV-1 long terminal repeat (LTR), oligonucleotide primers used to amplify viral transcripts, and the expected sizes of PCR products are shown in FIG. 2. The three primers, make up two primer pairs which amplify DNA to the lengths shown. U3, R, and U5 are regions of the HIV-1 LTR. TAR sequences form the first 59 nt of the R region, the start site for RNA transcription. The TAR fragments each have 59 base pairs and are amplified by the primer pairs 1 and 2. Full-length, polyadenylated transcripts amplify to 182 base pairs with primer pairs 1 and 3 which bracket the RU5 region of the LTR. The RU5 region is common to all elongated, full length viral mRNA. The respective lengths are diagrammed below LTR. A schematic representation of the control mRNA, the clone LTR*, shows its PCR-generated products to be 129 and 252 base pairs, as shown at the bottom of the FIG. 2.

FIG. 2 also shows the first primers set, primers 1 and 2 encompass the first 59 nucleotides (TAR) of all HIV mRNA species. The second primer set, primers 1 and 3, encompass the region corresponding to the first 182 nucleotides of HIV mRNA the RU5 region and detects all transcripts except for the TAR fragment. The signal obtained from each set of primers can be expressed as a ratio (the processivity ratio) that reflects the relative abundance of processive TAR-containing transcripts (mRNA+genomic RNA) relative to the total number of TAR-containing transcripts (mRNA+genomic RNA+TAR fragments). The processivity ratio measures the fraction of HIV transcripts successfully elongated into genomic and mRNA species. In the current assay, the final result is expressed as the processivity ratio.

The control long terminal repeat (LTR*) is a genetically-engineered clone of the LTR that contains 70 base pairs (bp) of heterologous DNA inserted into the TAR loop, between the binding sites for the primers 1, 2 and 3, described above. LTR* is used as the control for all steps employed in the procedure of the current invention and is included as an standard curve for each RT-PCR to achieve relatively precise quantitation.

To be able to detect the presence of TAR fragments, a reverse transcription-polymerase chain reaction (RT-PCR) assay was utilized using these novel primers and probes, as described above, to monitor the extent of processive transcription in both clinical and experimental HIV infections. In this modified RT-PCR, total RNA is purified from HIV-infected cells by disruption of the cells in a chaotropic buffer, such as one consisting of 8M urea, 2% SDS, 0.15M NaCl, and 0.1M Tris, pH 7.5, 0.001M EDTA. The cell disruption is followed by extraction with an organic solvent or mixture thereof, such as phenol/chloroform/isoamyl alcohol (50:48:2). The sample is then treated with DNase. The RNA is reverse transcribed into cDNA with random primers and analyzed by PCR with the two sets of primers described above. One set encompasses the first 59 nucleotides of all HIV RNA species (TAR); a second primer set amplifies the region corresponding to the first 182 nucleotides of HIV RNA and detects all transcripts except for the isolated TAR 59 bp, fragment as seen in FIG. 2. The signal obtained from each set of primers is then expressed as a processivity ratio that reflects the abundance of TAR-containing transcripts relative to the full length transcripts.

Because this assay relies on the quantitation of PCR product, a genetically-engineered clone of the HIV long terminal repeat (LTR*) was constructed that contains 70 base pairs (bp) of heterologous DNA inserted between the binding sites for the primers employed. This DNA was cloned into a "riboprobe" vector allowing the convenient in vitro synthesis of the modified LTR RNA, as seen at the bottom of FIG. 2. With LTR*, reverse transcription was demonstrated to be equally efficient on both regions to be amplified and both sets of primers supported PCR with equal efficiency. Results are seen in FIG. 8, left hand panel (8A). For the detection and quantitation of amplified product obtained from the different sets of primers, liquid hybridization of amplified product with a $^{32}$P-labeled probe followed by polyacrylamide gel electrophoresis and autoradiography was used as standard method of detection. While this method is extremely sensitive, quantitation can be complicated by variability in the hybridization of probe to differing amounts of amplified product probably due to strand displacement of probe when higher concentrations of amplified product are present in the hybridization. More direct methods of detection such as Southern blotting, digoxigenin-labeled amplified product followed by chemiluminescent detection by commercially-available techniques can also be suitably used.

FIG. 3 illustrates the method used to detect nonprocessive and processive HIV gene expression which is the basis of this invention. This analysis relies on the detection of different HIV transcripts with appropriately designed primers. Primer sequences are listed above and in the figure. One set of primers, primers 1 and 2 or SL0–SL4, encompasses the first 59 nucleotides of TAR present in all HIV RNA species including TAR fragments and full length transcripts (FIGS. 2 and 3A and B).

A second primer set, primers 1 and 3, or SL0-U5.1, amplifies the region corresponding to the first 182 nucleotides of HIV RNA and detects all transcripts except for the TAR fragment (FIG. 3B). The ratio of the signals generated by these two primer pairs reflects the abundance of the TAR fragments relative to genomic and mRNA species. A control RNA (LTR*) was constructed to monitor the efficiency of amplification with each respective primer pair (FIG. 3). This control was generated by the insertion of heterologous sequences between the primer binding sites for SL0 primer 1 and both downstream primers SL4 and U5.1. Patterns of RNA expression were evaluated in a cell model of HIV latency (ACH2) and in PBMC from both asymptomatic and AIDS patients. SL0/SL4 (primer set A) detects TAR+ mRNA, SL0/U5.1 (primer set B) detects mRNA only. Therefore, if the ratio of the signals generated by set A to set B is higher than 10:1, there is an excess of TAR and the HIV transcription is nonprocessive. If the ratio is smaller than 10:1, then the full activation of the processive transcription is indicated.

FIG. 4 shows the structure of retroviral vectors. As background to the development of our invention, it was necessary to study the molecular basis of HIV latency in vivo, and to determine whether Tat rather than Rev is responsible for HIV activation. Studies in which Tat or Rev were added to a tissue culture model of cellular latency (U1 cell line) were performed to see if Tat is the rate limiting factor in the induction of HIV-1 proviruses in U-1 cells. Results are shown and discussed in FIGS. 4–6.

Although the progression from sero-conversion to the acquired immune deficiency syndrome (AIDS) frequently takes years, viral replication occurs at all stages of the infection. In particular, high levels of virus can be detected in lymph nodes during the asymptomatic stages of disease progression. Nonetheless, the fact that there is persistent replication of HIV even in early stages of clinical latency does not mean that individual cells do not harbor latent proviruses causing cellular latency. Indeed, individual infected cells harbor proviruses that are not expressed until further cellular activation. Moreover, large numbers of latently infected cells can be detected both in lymph nodes and in the blood before the actual onset of AIDS.

Since both cellular and viral factors may contribute to the maintenance of cellular latency, studies were performed in a tissue culture model of HIV-1 latency using U1 cells. Proviruses of U1 cells are poorly expressed until cellular activation is initiated by a number of cytokines/lymphokines or phorbol esters that act through the cellular transcription factor NF-KB. U1 cells are derived from U937 cells which represent immature human CD4-positive monocytes, and contain two integrated HIV-1 proviruses.

The activation of U1 cells by phorbol esters has been shown to increase levels of total viral RNA and especially of larger singly-spliced and unspliced viral transcripts. To determine if the maintenance of proviral latency in U1 cells is due to insufficient levels of a viral gene product, specifically Tat or Rev, it was determined whether or not increased expression of Tat or Rev from heterologous promoters provided by retroviral vectors could induce these proviruses in U1 cells. To this end, retroviral vectors that expressed either Tat or Rev were constructed (FIG. 4) using the genome of the murine leukemia virus (MuLV). High titer viral stocks were obtained that could infect human epithelial and lymphoid cell lines and transfer functional Tat or Rev into these cells.

Vectors shown in FIG. 4 were based on the MuLV genome as described in *AIDS Res. Human Ret.*, 10:47 (1994). Open boxes represent the long terminal repeats; black boxes represent the SV40 early promoter; striped boxes are either the tat cDNA or the rev cDNA; and NEO is the G418-resistance gene. Controls for the function of these vectors was as follows: a 50-fold increase in chloramphenicol acetyl transferase (CAT) activity in U937 cells infected with LtatSN compared with U937 cells infected with LXSN when both were transiently transfected with a plasmid containing an HIV-1 LTR 5' to the cat gene. There was over a 200-fold increase in p24$^{gag}$ in U937 cells infected with LrevSN compared with U937 cells infected with LrevSN when both were transiently transfected with a HIV-1 provirus containing a frame-shift mutation in the second exon of Rev.

FIG. 5 shows the effect of Tat and Rev on the expression of viral proteins in U1 cells. Tat expression induces the HIV-1 proviruses in U1 cells in the absence of cellular activation.

U1 cells were grown in RPM1 with 10% calf serum and antibiotics. PBMC were separated from anticoagulated whole blood with Sepracell-MN obtained from Sepratech, Oklahoma City, Okla. When cultured, 4×10$^6$ cells were added to 4 ml of RPMI with 20% fetal bovine serum, 5% interleukin-2, and 0.12% polybrene. The mitogens 1 μg/ml PHA and 50 ng/ml PMA were added to the medium to stimulate U1 cells when desired.

FIG. 5 shows infection of U1 cells with retroviral vectors containing Tat (LtatSN) or rev (LrevSN) and with wild-type MuLV. 1×10$^6$ U1 cells were infected with 2×10$^5$ G418 transforming units of virus for LtatSN and Lrev SN or with 1×10$^6$ TCID$_{50}$ units of wild-type MuLV. An aliquot of cells was also treated with PMA/PHA. The Y-axis is a logarithmic scale. Symbols: LtatSN infected cells, closed circles; LrevSN infected cells, open circles, wild-type amphotropic MULV infected cells, closed squares; and PHA/PMA treated cells, open squares.

U1 cells were transduced with either the Tat or Rev retrovirus vectors as seen in FIG. 4, and the levels of HIV-1 expression were monitored by measuring levels of secreted p24$^{gag}$ in the culture supernatant (FIG. 5A). Control consisted of either mock infections or infections with the wild-type amphotropic —■— to control for possible effects of MuLV proteins in U1 cells. FIG. 5 panel A shows that Tat but not Rev brings U1 cells out of latency to the same extent as PMA/PHA.

Infections of U1 cells with the wild-type MuLV and the retroviral vector encoding Rev did not increase levels of p24$^{gag}$. On the other hand, infections with the retroviral vector encoding Tat led to rapid and sustained increased in levels of p24$^{gag}$. By day eight after infection, these levels were 100-fold higher than in the control U1 cells, and were nearly equivalent to those observed with PMA (FIG. 5A). This induction of p24$^{gag}$ by Tat was nearly equivalent to that observed with PMA (—☐—).

FIG. 5, panel B represents a Northern blot of RNA extract from the treated U1. Seven days after infection, RNA was collected from cultures infected with the same retroviral vectors as in Panel A. 10 μg of total RNA was loaded per lane. Lane 1 were unstimulated U1 cells; lane 2 were U1 cells infected with LtatSN; lane 3 were U1 cells infected with LrevSN; lane 4 were U1 cells infected with wild-type MuLV. Sizes of the major RNA species, which represent genomic, env, and multiply spliced viral transcripts were used as markers and are marked.

Uninfected U1 cells express small amounts of doubly-spliced viral mRNAs (FIG. 5b, lane 1). Tat alone increased both the total amounts of viral RNA, and increased levels of singly-spliced and genomic viral transcripts relative to those of doubly-spliced mRNAs (FIG. 2B, lane 2). On the other hand, the quantity and splicing patterns of these mRNAs did not change when rev or neo genes were introduced into these cells (FIG. 5B, lanes 3 and 4). The data described in FIGS. 5A and B confirm that constitutive expression of Tat induces the expression of integrated proviruses and can substitute for cellular activation of U1 cells.

FIG. 6 further illustrates effect of Tat on expression of viral proteins and viral spread in U937 cells infected with HIV$_{Lai}$.

Constitutive expression of Tat accelerates viral spread. U937-tat (circles), U937-rev (triangles) and U937-neo (squares) were infected at day 0 with HIV at a multiplicity of 0.1. Cell-free culture media was collected every 3–4 days and the cells were split 1:2. Levels of p24$^{gag}$ were measured by ELISA (Coulter Immunologics) with standards provided with the kit.

To ensure that these observations on effects of Tat also pertained to the wild-type, fully infectious HIV-1 cells, which are the parent of U1 cells, were infected with the Lai strain of HIV-1. Since HIV-1$_{Lai}$ grows slowly in U937 cells, it was expected that if virus replication were limited by the quantity of Tat in these cells, then exogenous Tat should increase the rates of viral spread. Indeed, HIV-1$_{Lai}$ spread more rapidly in cells that constitutively expressed Tat than in cells that expressed Rev or control cells expressing only Neo as seen in FIG. 6. Thus, levels of Tat are rate-limiting for the maintenance of viral latency and also for rapid viral spread in these promonocytic cells.

From the above studies, it is clear that constitutive expression of the viral protein Tat induces the expression of all major viral transcripts and proteins in U1 cells, whereas the viral protein Rev has no effect. This suggests that latency is maintained in U1 cells because of a lack of Tat protein. A reverse transcription-polymerase chain reaction (RT-PCR) method was developed to detect the short, promoter-proximal transcripts that are made from the viral LTR in the absence of Tat, and it was showed that U1 cells synthesize large amounts of promoter-proximal transcripts relative to promoter-distal transcripts. Cellular activation with phorbol esters, or introduction of Tat alone, increased the relative abundance of promoter-distal transcripts, indicating that Tat may be the pivot viral protein in the maintenance of latency.

To determine whether Tat induces all viral mRNA in U1 cells was investigated by studies described in FIG. 7.

FIG. 7 is a Northern blot of RNA from U1 cells, as described below. The Northern blot shows that Tat induces all major classes of viral mRNAs in U1 cells. 7 days after infection, RNA was collected from cultures infected with the same retroviral vectors as in FIG. 5. RNA was also extracted from U1 cells stimulated with PHA/PMA for 48 hours.

FIG. 7, panel A, lane 1 shows unstimulated U1 cells, lane 2 shows U1 cells infected with LtatSN; lane 3 shows U1 cells infected with LrevSN; lane 4 shows U1 cells infected with wild-type MuLV. Panel A was exposed for 1 day. FIG. 7, panel B, lane 1 shows U1 cells stimulated with PMA/PHA; lane 2 shows U1 cells infected with LtatSN.

Sizes of the major RNA species, which represent genomic (11 kb), singly-spliced env (4 kb) and doubly-spliced (2 kb) viral transcripts, are marked. The radiolabelled probe contained the entire HIV-1 LTR and the first 500 bp of gag.

FIG. 7 illustrates results obtained by the introduction of Tat or Rev into U1 cells and extraction of total RNA from equal number of U1 cells 7 days after infection with above described retroviral vectors. Uninfected or mock infected U1 cells expressed small amounts of doubly-spliced viral mRNA, FIG. 7A, lane 1. The quantity and splicing patterns of these mRNAs did not change when rev or neo genes were introduced into these cells as seen in FIG. 7A, lines 3 and 4. Introduction of Tat induced all species of viral mRNAs, as seen in FIG. 7A, line 2 and in FIG. 7B, line 2. These levels were lower than those obtained with PMA as seen in FIG. 7B, lane 1.

In addition to increasing total amounts of viral RNA, Tat increases levels of singly-spliced and genomic viral transcripts relative to those doubly-spliced mRNAs, as illustrated by comparison of FIG. 7A, lane 2 and FIG. 7B, lane 2. These studies again confirm that Tat is involved in viral transcription.

This invention is based on findings confirmed by the above studies that Tat protein rather than Rev is involved in regulating viral latency. We then discovered the evidence that Tat protein is inhibited or absent in vivo, in HIV infected individuals. During the latent stage of infection in HIV positive asymptomatic subjects, there is an accumulation of TAR fragments and a paucity of full length transcripts. Full length transcripts appear only in the presence of Tat protein and are seen as more virus becomes activated, a phenomenon that peaks in subjects with advanced disease. Therefore, the ratio of TAR fragments to full length transcripts reflects the degree of latency and viral replication.

To determine levels of TAR fragments and full length viral transcripts in patient samples and cell line models of latency, quantitative RT-PCR was used. We first studied transcription in activated and Tat-infected U1 cells. Results are illustrated in FIG. 8.

FIG. 8 illustrates detection of transcripts initiated from the HIV-1 LTR in U1 cells by RT-PCR and continue the work reported above on U1 cells. Panel A is the standard curve generated by dilutions of LTR*. The TAR fragments and full-length, polyadenylated transcripts are revealed by primer pairs 1 and 2 and 1 and 3, respectively of both the LTR* and sample RNA as diagrammed in FIG. 2. Panel B shows ratios of short (SA) to long (LT) transcripts in U1 cells infected with retroviruses encoding Tat or treated with PHA/PMA. RNA from U1 cells was amplified with the primer pairs shown in FIG. 2. Days following activation are as follows: d0 are non-activated U1 cells; TAT d4 and d8 are U1 cells 4 and 8 days after infection with LtatSN (FIG. 4); PMA/PHA d4 are U1 cells 4 days after stimulation with PHA and PMA. The ratio of the long transcripts (LT) to short transcripts (SA) is shown under each lane.

In this study, pairs of primers that correspond to 5' and 3' ends of TAR (primer 1 and 2 and to the 3' end of the U5 region (primer 3) were synthesized (FIGS. 3 and 4). Primers 1 and 2 would amplify both TAR fragments and full length transcripts, while primers 1 and 3 would amplify only RNA that was only full length and longer than the TAR region (FIG. 8A), that is, only full length transcripts would be amplified. Given the steep transcriptional polarity in the absence of Tat, and the fact that only prematurely terminated transcripts which contain the TAR RNA stem-loop are stable in cells, the second set of primers (1 and 3) detects very few, if any, prematurely terminated transcripts. Both sets of primers amplified with equal efficiencies in vitro transcribed RNA and plasmid DNA, and was sensitive to <100 copies of nucleic acid (FIG. 8A).

Proportions of short to long transcripts were assessed by comparing autoradiographs of amplified DNA obtained with both sets of primers (FIG. 8B, left). Non-activated U1 cells transcribed predominantly TAR fragments (FIG. 8B-d0). This correlated with the low levels of doubly-spliced transcripts in U1 cells as seen in FIG. 7B, lane 1. However, four and eight days after infection with amphotropic retroviruses coding for Tat (FIG. 4), ratios of short to long amplicons decreased by 10- to 100-fold (FIG. 8B, central lanes). Moreover, four days after the administration of PHA/PMA, the ratios of short to long amplicons decreased similarly (FIG. 8B, right hand lane). Activation of U1 cells with PMA led to a more rapid qualitative change in HIV-1 transcription, which suggests that activated U1 cells expressed Tat earlier than those infected with amphotropic retroviral vectors. These experiments suggest that the escape from viral latency is accompanied by Tat mediated increase in elongation efficiency of RNA polymerase II.

FIGS. 9–12 illustrate results obtained in asymptomatic HIV positive or in AIDS subjects.

FIG. 9 shows the ratio of short transcript/long amplicons (SA/LA) regions in one HIV patient's samples. The patient was asymptomatic (CD4+=420) male. PBMC were obtained from his blood sample and treated according to procedure of Example 1 and 5. Primers and control mRNA were described above. The materials used for this sample as well as those for the subsequent figures are as follows. RNA was purified from cell lines and from patient samples by acid phenol extraction in the presence of UNSET buffer which contains 8M urea, 2% sodium dodecyl sulfate (SDS), 0.1 M Tris-HCl, pH 7.5, 0.15M NaCl, 0.1 mM EDTA. Following precipitation of nucleic acids with ethanol, the sample was resuspended in 20 µL of diethyl pyrocarbonate (DEPC)-treated water. cDNA was synthesized in 20 µL volume containing 0.5 mM of each dNTP, 10 mM DTT, 20 U RNase inhibitor (Boehringer Mannheim), 10 pmol of random hexamers (p(dN)6, Pharmacia-LKB Biotechnology) and 200 units of Moloney Murine Leukemia Virus Superscript reverse transcriptase obtained from Bethesda Research Laboratories, Gaithersburg, Md. The RT mixture was incubated for 10 minutes at room temperature, followed by 42° C. for 1 hour. To degrade template RNA after cDNA synthesis, 0.5 units of RNase H (Bethesda Research Laboratories, Gaithersburg Md.) were added and incubation was continued at 37° C. for 40 minutes, followed by 90° C. for 5 minutes.

A commercially available PCR carry-over prevention kit (Perkin Elmer-Cetus Corp., Norwalk, Conn.) was routinely used for all PCR amplifications. The cDNA preparations were amplified in a final volume of 50 µL in a thermal cycler (Bios stuff) for 30 cycles. The amplification mixture contained 1U AMPLITAQ (Perkin Elmer-Cetus Corp., Norwalk, Conn.), 1U Uracil n-glycolysase, 35 pmol of each primer, 200 uM each DATP, dGTP, dCTP and dUTP, 10 mM Tris (pH 8.3), 3 mM $MgCl_2$, 50 mM KCl, and 200 µg/ml gelatin. The thermal profile was 95° C. for 30 seconds, 72° C. for 40 seconds and 56° C. for 20 seconds.

Specific amplified products were detected by oligomer hybridization using $^{32}$P-labeled probes directed to the TAR loop and the LTR* loop region (FIG. 3) according to the protocol described in PCR Protocols: A Guide to Methods and Applications, editor Innis M A, Gelfand D H, Sninsky J T, White T., New York: Academic Press, pages 337–347 (1990). Hybridization was followed by polyacrylamide gel electrophoresis and autoradiography as described.

FIG. 9 shows the autoradiograph illustrating the ratio of SA to LA using primer set A/primer set B SL0/SL4:SL0/U5.1 and the TAR probe. In fresh undiluted PBCM (Panel A) ratio of more than 1000:1 of SA/LA was found. In this case, there was no detectable level of full length transcripts. When the sample was stimulated with mitogens for 3 days and with activated Feeder Cells for two weeks, the ratio of SA/LA decreased significantly. This was due to the increase processive transcription following activation of the virally infected cells by mitogens. The virus infecting these cells were latent in the fresh sample but fully competent to replicate following activation.

In summary, both the cell line models of HIV latency and this asymptomatic HIV+ subject showed a predominance of TAR fragments during latency and the appearance of full length transcript following activation. FIG. 9 clearly shows that in the PBMC from an asymptonatic HIV positive patient, the TAR fragments, amplified by primer pair A: SLO/SL4 was very abundant while the full length transcript, amplified by primer pair B: SL0:U5.1 was undetectable (FIG. 9, panel A). Two other methods of stimulation activated viral gene expression in these latently-infected cells and both resulted in significant decrease in the ratio of short to long transcripts (FIG. 9, panels B and C).

When the current assay was run, under the same conditions (FIG. 10), in the PBMC of an AIDS patient with CD4+=36/mm$^3$, the ratio of SA/LT was between 1:1. As seen in the FIG. 10, there was a large number of long amplicons. The PBMC of this AIDS patient also demonstrated a very low ratio (1:1) of short to long amplicons (FIG. 10) indicating the almost exclusive presence of processive transcription.

This study confirms that there is a difference in the processivity ratio of asymptomatic HIV positive subjects and those subjects who have progressed to the AIDS stage. The processivity (SA/LA) ratio is therefore a viable diagnostic tool for detection of HIV transcriptional activity.

To determine whether Tat is critical for viral latency in HIV infected individuals as it has been shown to be in cells, further studies were performed in PBMC obtained from HIV infected individuals using the RT-PCR method as described above and in examples.

To this end, RNA was extracted from PBMC of subjects throughout the course of the disease including early after infection and terminally-ill AIDS patients. In all infected individuals, transcriptionally active proviruses were detected with promoter proximal probes (primer set A) as shown in FIGS. 9 and 10. However, the proportion of TAR fragments to full length transcripts changed with advance in disease.

FIG. 11 shows the presence of HIV-1 transcripts in PBMC of four infected individuals. RT-PCR products from PBMC of infected but asymptomatic (CD4 counts of 420 and 412) and AIDS patients (CD4 counts of 10 and 36) are shown. The asymptomatic patients were Walter Reed stage I and were not receiving anti-viral therapy at the time the blood was taken. The AIDS patients were Walter Reed stages V and VI and were receiving AZT at the time the blood was taken. PBMC from one asymptomatic patient (CD4 count 420) were activated with PHA/PMA for three days with PHA and or by con-cultivation with feeder cells for fourteen days. Ratios of long to short amplicons (LA:SA) were estimated as in previous figures and are shown under each lane.

Although PBMC from one asymptomatic patient contained abundant TAR fragments, no full length transcripts could be detected (FIG. 11-A, CD4 count 420). However, three days after mitogenic stimulation (d3), or fourteen days (d14) after co-cultivation with stimulated feeder cells, ratios of short to long amplicons declined to less than ten-fold (FIG. 12, left hand panels). Levels of long transcripts, which were observed after cellular activation, were correlated with the appearance of $p24^{gag}$ in culture supernatant (undetectable, 9 pg/ml and over 100 pg/ml on days 3, 7, and 14 after cellular activation, respectively). These data suggested that all or nearly all proviruses in PBMC of this infected individual were latent, and moreover, his cells appeared like non-activated U1 cells (compare FIG. 8B).

Decreased ratios of short to long amplicons were observed in another asymptomatic infected individual (FIG. 11-B, CD4 count 412). As this analysis represented RNA from large populations of cells, it reflects the overall state of virus replication in this subject's PBMC. It appears that this asymptomatic individual is in the state of transition from latency to activation. On the other hand, both AIDS patients (FIGS. 12-C and 12-D) had lower ratios of short to long amplicons, and an equal number of short and long amplicons were observed in PBMC of one patients (FIG. 11-D, CD4 count 36). Therefore, increased levels of full-length transcripts correlated with the progression of clinical disease. Thus, the relative paucity of full length transcripts marked viral latency not only in U1 cells but in cells from infected individuals and increasing levels of full length transcript mark the viral activation and disease progression.

Because of the concordance between assays of Tat function and RT-PCR in U1 cells, RT-PCR was used to detect this form of proviral latency in peripheral blood mononuclear cells (PBMC) from HIV-1 infected individuals in the extremes of CD4 cell counts (FIG. 12). To this end, RNA and DNA was extracted from PBMC of 9 HIV-1 infected individuals having high CD4 levels (CD4 cells/mm$^3$ ranged from 1051 to 502 with a median level of 620). None of these individuals was viremic, and all were asymptomatic except for oral candida in two individuals. CD4 are the lymphocytes responsible for cell mediated immunological reaction. When their count is high, individual possess a reasonably well-functioning immune system. When their count is low, the immune system is destroyed and AIDS result.

FIG. 12 illustrates analysis of HIV-1 transcripts in PBMC of infected individuals with high CD4 counts. RNA and DNA was isolated from buffy coats of individuals labelled 1 through 9 in panels A, B, C, and D and subjected to PCR in the presence or absence of reverse transcriptase as described above and in Examples.

Panel A represents results obtained by RT-PCR with primer pair 1 and 3 for full length transcripts using the RNA extracted from the PBMC of individuals 1–9. The lane marked U1 is RNA from activated U1 cells. As expected, no long amplicons were found in these individuals, who were all in latent asymptomatic stage of the HIV infection.

Panel B is RT-PCR with primer pairs 1 and 2 for TAR fragments using the same RNA template from the PBMC of individuals 1–9. The lanes marked U1 are RNA from activated U1 cells. The minus or plus sign indicates whether or not reverse transcriptase was added to the reaction prior to the PCR and is a control for DNA contamination. As expected, the presence of abundant short amplicons in all patients is seen when reverse transcriptase is added. When reverse transcriptase was omitted, no formation of short amplicons was observed.

Panel C is PCR with primer pairs 1 and 3 using DNA extracted from the PBMC of individuals 1–9. HL60 is DNA from HL60 cells is used as negative control.

Panel D is PCR with primer pairs 1 and 2 using a DNA templates from the PBMC of individuals 1–9. This proves the virus infecting these individuals had DNA sequence compatible with our primers and probes.

In all nine cases the presence of promoter-proximal transcripts could be readily detected (FIG. 12B) in the absence of promoter-distal transcription (FIG. 12A). Controls of the reactions without reverse-transcriptase verified that the promoter-proximal signal was due to RNA rather than DNA (FIG. 4B, lanes marked with a minus sign). This result indicates all (9/9) of these HIV positive non-AIDs individuals with high CD4 counts harbored latent proviruses that were transcriptionally active, but deficient in transcription elongation. In patients with high CD4 counts, there is the exclusive presence of promoter proximal transcript.

UTILITY

HIV is able to establish latent infection in which infected cells demonstrate extremely low level of gene expression and viral replication. Tat is known to be an essential gene for viral replication and it is the key viral element for up-regulating HIV gene expression. Therefore, control of Tat levels or function may play a part in the establishment and maintenance of latent infection. In vitro, Tat has been clearly shown to be involved in the switch from latent to active infection. Tat binds to the initial sequence of the viral RNA, the TAR element, where it interacts with a variety of cellular proteins that mediate transcription.

The regulation of Tat function significantly affects levels of HIV gene expression in vivo and contributes to a clinically latent state. Evidence of this was obtained in the form of excess TAR fragments in the absence of full length transcripts which represent signature of deficient Tat function in PBMC from 10 of 11 asymptomatic individuals.

Tat functions as a processivity factor, stabilizing the RNA polymerase complex as it continues transcription beyond the initial TAR region of the transcript. In cell lines infected with Tat-defective mutants of HIV, there is an accumulation of the short TAR transcripts which are thought to be the primary or processed product of abortive initiation events. With the addition of Tat protein, transcription is not aborted and the TAR containing transcripts are elongated into viral mRNA species.

Utilizing a reverse transcription-polymerase chain reaction assay (RT-PCR) with novel primers and probes it has been found that the unique small RNA transcript encoding the transactivator (TAR) element of human immunodeficiency virus) is present in infected peripheral blood mononuclear cells from asymptomatic subjects. The finding of abundant TAR fragments in asymptomatic subjects makes it a good target for an early detection of HIV infected cells.

In addition, the discovery has been made that the proportion of the TAR fragments to all other viral mRNA decreases following activation. Since the transition from the synthesis of TAR fragments to full length transcripts may be one of the earliest events of the course of viral infection and may reveal significant changes in patterns of viral gene expression and replication far in advance of other clinical manifestations of infection. Knowing the type and degree of HIV transcription allows for early detection of the transition from the latent to the acute state of disease, a moment of great significance in the evolution of the disease.

The primary utility of the current invention is to provide a sensitive tool for detection of HIV transcription, a measure of the load of latently infected cells and a sensitive indicator of the transition from latent to active stage of the HIV replication.

Several novel features were added to the standard RT-PCR technique that reflect the nature of the discovery, namely, the method and assay include the calculation of the difference and a ratio, specifically designed sets of primers for detection of TAR fragments and other full length transcripts viral RNAs, the hybridization probe sequences, the internal control sequence, and the use of short amplicons and long amplicons to calculate a difference and a ratio to determine states of the viral latency and activation.

The new marker, method and assay of this invention can be used to detect HIV infection and monitor viral activity. The relatively high copy number of TAR sequences, present in both latently-infected and actively productive cells as the initiating sequence of all RNA species, makes it a good target for nucleic acid-based assays for HIV detection. The size differences between the TAR fragments found in latency and full length transcripts found following activation has been exploited to provide information about the state of viral activation. For example, lymphocyte subsets can be examined to determine the state of viral activity in different cell types. The assay is also clinically useful. Discreet states of viral activation can be defined with this assay and, the course of the disease can be sensitively monitored, resulting in identifying the progression of infection before other indicators of viral progression have changed and in the absence of clinical symptoms. The assay could also be used evaluate and monitor anti-viral agents for their ability to suppress viral replication and gene activity.

The current invention has prognostic significance. Individual absolute levels of TAR fragments may predict disease course early after seroconversion as well as the proportion of short to long transcripts predicting the transition from latency to activation. These parameters provide effective tools for determining the rate at which individuals progress.

Due to the ability of the HIV virus to establish latent infection with low DNA copy number and little gene expression, direct markers of viral presence or gene expression, such as viral DNA, RNA and protein, have been heretofore difficult to demonstrate. The currently available tests for direct viral detection are the p24 antigen ELISA assay or PCR for viral nucleic acids. Only the p24 ELISA assay is easily done and it is an insensitive test. Assays for viral nucleic acids are difficult and expensive to perform. All other routine assays available to monitor HIV disease are directed to monitoring the response of the immune system to the virus (T cell subsets, neopterin, etc.). However, the newly provided assay which includes novel primers and probes will allow this assay to be practiced in every biochemical laboratory.

The relatively high copy number of TAR fragments that the new method and assay are able to detect and distinguish in both latently infected and actively productive cells makes it a good target for nucleic acid-based assays for HIV. With the further development of solid phase branch chain DNA and flow technologies for the detection of specific nucleic acids, the TAR sequence will be a valuable marker both of viral presence and of viral expression.

EXAMPLE 1

A Reverse Transcription Polymerase Chain Reaction for Monitoring HIV Recessive Transcription in HIV Infections This example illustrates development of a reverse transcription-polymerase chain reaction (RT-PCR) assay with novel primers and probes to detect and monitor the extent of non-processive and processive transcription in both clinical and experimental HIV infections.

RNA was isolated from $2 \times 10^6$ cultured cells or freshly isolated PBMC as described in *Hepatology*, 17:188 (1993). Harvested cells were resuspended in urea lysis buffer (8 M urea, 2% SDS, 0.1 M Tris-HCl, 0.15 M NaCl, 0.1 mM EDTA, pH 7.5), and further extracted by a mixture of phenol/chloroform/isoamylalcohol (50:48:2). Following precipitation with ethanol, samples were treated with 10 URNase-free DNase I in a buffer consisting of 100 mM Na acetate, 5 mM $MgCl_2$, pH 5.4 for 1 hour at room temperature. To determine if sequence variabilities or the addition of DNase I could affect efficiencies of amplification of RNA from PBMC, aliquots of purified samples were also removed before DNase I treatment and amplified with each primer pair. Finally, RNA was serially diluted with water, that had been treated with DEPC and contained 1 mg/ml of tRNA.

cDNA synthesis was performed with random primers in a 20 μl reaction mix consisting of 0.5 mM of each dNTP, 10 mM DTT, 20 U RNase inhibitor, 10 pmol of random hexamers (p(dN)6, and 200 units of MuLV Superscript reverse transcriptase (Bethesda Research Laboratories, Gaithersburg, Md.). The RT mixture was incubated for 10 minutes at room temperature, followed by 42° C. for 1 hour. To degrade template RNA after cDNA synthesis, 0.5 units of RNase H (Bethesda Research Laboratories, Gaithersburg, Md.) were added and the incubation was continued for 40 minutes at 37° C., followed by 5 minutes at 90° C.

A commercially available PCR carry-over prevention kit AMPLIWAX (Perkin Elmer-Cetus Corp., Norwalk, Conn.) was also added to each sample. cDNAs were amplified in a final volume of 100 μl in an amplification mixture containing 1 U AMPLITAQ (Perkin Elmer-Cetus Corp., Norwalk, Conn.), 1 U Uracil n-glycolysase, 0.8–1.0 pmol of each primer, 200 uM each DATP, dGTP, dCTP and 100 μM dUTP, 10 mM Tris (pH 8.3), 3 MM $MgCl_2$, 50 mM KCl, and 200 μg/ml gelatin, for 30 cycles in a BIOS-cycler (Bios Corp., New Haven, Conn.) using a thermal profile for 20 seconds at 95° C., for 20 seconds at 56° C. and 40 seconds at 72° C. Sequences of primers and probes were derived from the $HIV_{Lsi}$ LTR. There were:

Primer 1: GGGTCTCTCTGGTTAGA (SEQ. ID No: 2)

Primer 2: GGGTTCCCTAGTTAGCC (SEQ. ID No: 3)

Primer 3: GGGCGCCACTGCTAGAGATT (SEQ. ID No: 4)

The amplified product of primer set 1 and 2 was 59 bp in length and the product of primer set 1 and 3 was 182 bp in length. Amplified products were detected by liquid hybridization as described in *AIDS*, 5:683 (1991). Each sample was separately amplified but hybridized together and electrophoresed together in 10% nondenaturing polyacrylamide gels for ease of comparison. The radiolabelled probe was complementary to the TAR loop region of the HIV-1 LTR:

TAR loop probe: AGACCAGATCTGAGCCTGGGAGCTCTCTGG (SEQ ID NO: 5)

This probe is hybridized to the amplified products of both primer sets, each of which contains the TAR stem-loop. This is a labeling technique that increases the specificity of the assay.

The probe was end-labeled with $\gamma^{32}P$ ATP and added to a final concentration of 30 pmoles to samples that were denatured for 1 minute at 95° C. and hybridized for 3 minutes at 56° C.

Additionally, two other probes were synthesized. The LTR* loop probe having sequence 5' GTGGCGGCCGCTCTAGAACTAGTGGATCCC '3 (SEQ ID No: 6)

for hybridization to the LTR* control amplified products, which have a different loop region; and the concatamerization probe, the TAR-linking probe having sequence:

5'CTCGAGAGACCGATTGATCCCT-
TGGGTTTCCCAGAGAGACCAATCTG-
GTCTAGACTCGGACC '3 (SEQ ID No: 7).

EXAMPLE 2

Preparation of U937, PBMC and U1 Cells

This example illustrates a procedure used for preparation of U937, U1 cells and PBMC used in studies supporting this invention.

U937 and U1 cells were grown in RPMI with 10% fetal calf serum and antibiotics. HeLa-CF4-LTR-β-gal cells were grown in DMEM with 10% calf serum, 0.2 mg/ml G418 and 0.1 mg/ml hygromycin. U937-tat, U937-rev, and U937-neo cells were derived by infection with the corresponding retrovirus vectors. LXSN, LtatSN and LrevSN, shown in FIG. 4, were selected in 1 mg/ml of G418. After selection for approximately 1 month, they were subsequently removed from G418. In all cases, frozen cells from early after infection were thawed and used for above experiments. The presence of Tat in U937-tat cells was verified by transient transfection of these cells with plasmids containing the HIV-1 LTR (PHIV CAT). 50-fold increase in CAT activity in the U937-Tat transfected cells was observed compared to the U937-neo transfected cells. The presence of Rev in U937-rev cells was verified by transient transfection with a plasmid containing a frame-shift mutations in the second exon of Rev as described in *J. Virol.*, 63: 4875 (1989), followed by measurement of p24$^{gag}$ in the cell-free culture medium by an ELISA (Coulter Immunologics). There was an over 200-fold increase in $p_{24}{}^{gag}$ in U937-rev cells compared to U937-neo cells.

PBMC were separated from anticoagulated (Acid-Citrate-Dextrose) whole blood with Sepracell-MN (Sepratech, Oklahoma City, Okla.). 4×10$^6$ cells were added to 4 ml of RPMI with 20% fetal bovine serum, 5% interleukin-2 (Cellular Products, Buffalo, N.Y.), and 0.12% Polybrene. For direct stimulation of PBMC or U1 cells, 1 μg/ml PHA plus 50 ng/ml PMA were added to the medium. Production of HIV-1 was measured by the p24$^{gag}$ ELISA as above.

EXAMPLE 3

Methods for Growth and Amplification of HIV Virus

This example illustrates methods used for growth, amplification and infection of U1 cells with retroviral vectors LXSN, MuLV, LrevSN and LtatSN used for cells studies.

HIV-1$_{LAI}$ was grown by transfection of pLAi according to method described in *Virology*, 185: 661 (1991) into HeLa cells. Virus was then amplified by serial passages for about 10 days in CEM cells and then frozen in small aliquots and tittered on HeLa-CD4-LTR-β-gal cells. Viral titers were typically about 2×10$^5$ infectious units per ml.

Amphotropic MuLV (strain 4070A) was amplified on NIH3T3 cells. The virus was tittered by serial end-point dilutions. Retroviral vector LXSN has been described in *Biotechnigues*, 7:980 (1989). LtatSN and LrevSN were made by inserting genomic fragments from the HIV-1$_{SF2}$ strain into the polylinker of LXSN and subsequent cloning of cells containing processed cDNAs for tat and rev, respectively. Producer cells were made as in amphotropic packaging lines as described in *Mol. Cell Biol.*, 6:2895 (1986).

U1 (1×10$^6$ cells) were infected with LtatSN, LrevSN or MuLV (each at a titer of approximately 2×10$^5$ on human cells) in a total volume of 500 μl of medium and 10 μg/ml polybrene for 2 hours at 37° C. The viral inoculum was washed away and replaced with 1 ml of RPMI with 10% fetal calf serum. Cells were not selected for G418 resistance. Cells were then split 1:2 every 3 to 4 days and aliquots removed for the analysis of p24$^{gag}$. Samples were frozen at −20° C. and analyzed simultaneously at end of each experiment.

EXAMPLE 4

Northern Blotting

This example describes Northern blotting method used in the experiments underlying this invention.

RNA was isolated from U1 cells by the lysis of cells with guanidinium isothiocyanate followed by centrifugation through a cesium chloride solution as described previously (Sambrook, Fritsch, and Maniatis, 1989). 10 μg of total RNA was loaded per lane on a formaldehyde-agarose gel, transferred to nylon filter, and probed with radiolabelled HIV-1 DNA.

EXAMPLE 5

An Assay and HIV-1 Processivity Determination Kit

This example describes an assay and a kit for detection of a processivity ratio of short transcripts to long transcripts.

Procedure includes the following steps:

I. Preparation of Cells

Cells were prepared as follows.

1. Whole blood (WB) was extracted into Acid-Citrate-Dextrose (ACD) tubes. One full tube (9 ml) yields approximately 20–30 micrograms nucleic acids. PBMC were isolated with Ficoll-Hypaque, washed 2 times in phosphate buffered saline (PBS) and cells were counted.

2. Aliquote 2×10$^6$ cells were transferred into a 1.5 ml eppendorf and pelleted in microfuge, 10,000 rpm, 3 minutes. At least 2 aliquots were made if DNA detection was performed.

3. Cell pellet can be frozen at this point at −70° C.

II. RNA Extraction

RNA was extracted by the following procedure.

1. Urea lysis buffer has the following compositions:

8M urea

2% SDS 0.1M Tris-HCl, pH 7.5

0.15M NaCl
0.1 mM EDTA

2. For each sample prepare 2.5 ml of UNSET urea lysis buffer was prepared as follows:

1.2 g urea
1 ml 2.5X UNSET salts (provided in kit)
water to 2.5 ml (approximately 0.6 ml)

3. 1.5 ml per sample of neutral phenol was equilibrated with equal volume of UNSET buffer and 0.2 (volume) of chloroform/isoamylalcohol (48:2).

4. Supernatant from PBMC pellet was aspirated and pellet was resuspended in 0.7 ml UNSET buffer and vortexed till pellet disappeared.

5. 70 µl 2M NaOAC and 0.84 ml equilibrated phenol was added to each sample.

6. Samples were vortexed 3 minutes then spun in microfuge at 10,000 rpm, 20 minutes, 4° C.

7. The supernatant was removed and re-extracted with an equal volume of equilibrated phenol.

8. Aqueous phase was precipitated with 2.5 volume EtOH and spin 30 minutes at 4° C., 9. Pellet was resuspended in 180 µl DEPC treated water containing 17 µl NaOAC (3M)
500 µl EtOH Sample can be frozen at this point.

III. DNase digestion

DNase digestion of samples for RNA analysis was performed as follows.

10X buffer: 1M NaOAC pH 5.2
0.05M $MgCl_2$

1. Sample was spun for 30 minutes and supernatant was aspirated and discarded.

2. Pellet was resuspended in 90 µl DEPC-$H_2O$.

3. 10 µl of 10X buffer and 3 µl DNase (4 mg/ml) were added.

4. The mixture was incubated for 1 hour at 37° C.

5. After incubation, the mixture was extracted 2X with phenol/chloroform (48:2).

6. 0.1 volume 2.5M NaOAC and 2.5 volume 100% ETOH were added.

Sample can be frozen at this point.

IV. cDNA synthesis

Synthesis of CDNA was according to the following procedure.

1. Sample was spun for 30 minutes, 10,000 rpm at 4° C.

2. Pellet was resuspended in 92 µl DEPC-$H_2O$ containing:

8.3 µl NaOAC (M)
250 µl 100% ETOH

3. The mixture was spun for 30 minutes and LTR* sample which is provided with kit was spun at the same time.

4. Sample was resuspended in 22 µl DEPC-$H_2O$. 10 µl was used for sample with reverse transcriptase (RT), 10 µl for sample without RT. LTR* was resuspended in 12 µl DEPC-$H_2O$.

5. With the remaining and 2 ||l, 3×10 fold serial dilutions of the sample RNA and 2×10 fold dilutions of the LTR* RNA into 8 µl DEPC-$H_2O$ were made.

6. The RT reaction mixture contains the following:

0.5 mM of each dNTP
10 mM DTT
20 U Rnase inhibitor (Boehringer Mannheim)
10 pmol of random hexamers (p(dN)6, Pharmacia-LKB Biotechnology)
200 units of Moloney Murine Leukemia Virus Superscript reverse transcriptase (Bethesda Research Laboratories, Gaithersburg, Md.)

For each 20 µl reaction, the following were mixed and added:

4 µl 5X RT buffer
1 µl DTT
0.1 µl dNTP
1 µl p(dN)6
2.4 µl DEPC-$H_2O$
1 µl RT
0.5 µl RNasin
10 µl sample 7. The mixture was incubated for 10 minutes at room temperature then 42° C. for 1 hour.

Sample can be frozen at this point.

8. To degrade template RNA after cDNA synthesis, 0.5 units of RNase H were added to each sample and to the sample reserved for DNA investigation.

9. The mixture was incubated at 37° C. for 40 minutes, followed by 90° C. for 5 minutes.

V. PCR

Target was amplified using PCR.

1. A PCR carry-over prevention kit and AMPLIWAX (Perkin Elmer-Cetus Corp., Norwalk, Conn.) was used for all PCR amplifications.

The cDNA preparations were amplified in a final volume of 100 µl using instructions for upper and lower reaction mixtures as provided by Perkin Elmer. The final amplification mixture contained:

1U AMPLITAQ (Perkin Elmer-Cetus Corp.)
1U Uracil n-glycolysase
70 pmol of each primer
200 µM each DATP, dGTP, dCTP and dUTP
10 mM Tris (pH 8.3)
3 mM $MgCl_2$
50 mM KCl
200 µg/ml gelatin The thermal profile was 30 cycles at 95° C. for 20 seconds, 72° C. for 40 seconds and 56° C. for 20 seconds.

VI. Liquid Hybridization

Detection of short and long amplicons was made by hybridization with labeled probes.

Specific amplified products were detected by oligomer hybridization using $^{32}$P-labeled probes directed to the TAR loop and the LTR* loop region (FIG. 3) according to the protocol described in *PCR Protocols: A Guide to Methods and Applications*, editors: Innis M A, Gelfand D H, Snisky J T, White T., Academic Press, New York, pages 337–347 (1990)). Hybridization was followed by polyacrylamide gel electrophoresis and autoradiography as described in the same reference.

VII. Evaluation of Results

Amplified products were quantified by determination of the final dilution at which signal is detected, and by comparison of signal intensity to the LTR* standard curve in its linear range. The absolute amount of total RNA and long transcripts was reflected by the signal intensity. The absolute amounts of short transcripts was reflected by the difference between the total RNA signal (SA) and the long transcripts signal (LA). The proportion of short transcript to long transcripts was reflected in a ratio of short to long amplicons (SA/LA). The ratio of SA/LA from 100:1 and above identified a subject to be in a latent stage. A ratio 10:1 and lower identified a subject to be in acute phase of HIV activation.

What is claimed is:

1. A method for assessment of HIV transcriptions activity and disease progression wherein nonprocessive transcription indicates viral latency and processive transcription indicates active viral gene expression, said method comprising steps:
   (a) determining the amount of TAR fragment by calculating a difference between an absolute level of total viral RNA transcripts and full length RNA transcripts or determining a proportion of short TAR fragments to full length RNA transcripts in infected cells of HIV positive subjects; and
   (b) correlating a change in said difference or proportion with disease progression;
   wherein the change in said difference or proportion indicates a transition from latency to activation and correlates with disease progression.

2. The method of claim 1 wherein said determined difference or proportion of TAR fragment to processive RNA transcripts in infected cells of HIV positive subjects is indicative of the relative amounts of nonprocessive and processive transcripts.

3. The method of claim 2 wherein the processive transcripts contain as a leader sequence the full sequence of the nonprocessive transcripts and detection of the leader sequence is equivalent to detecting total viral transcripts.

4. The method of claim 3 wherein a detection of a processivity ratio reflecting a ratio of total transcripts to processive polyadenylated transcripts larger than 1, indicating a greater level of TAR transcripts than full length viral mRNA, is correlated with and is indicative of nonprocessive HIV transcriptional activity.

5. The method of claim 4 wherein levels of nonprocessive HIV transcriptional activity indicate the degree of viral latency.

6. The method of claim 3 wherein a detection of a processivity ratio, reflecting a ratio of total transcripts to processive polyadenylated transcripts equals to 1, indicating an absence of TAR transcripts, is correlated with and is indicative of fully processive HIV transcriptional activity.

7. The method of claim 6 wherein a detection of a processive HIV transcriptional activity indicates viral activation.

8. A method for assessment of HIV transcriptional activity and disease progression wherein levels of nonprocessive transcription indicate degrees of viral latency and processive transcription indicates fully active viral gene expression and wherein changes in the absolute or relative amounts of processive and nonprocessive transcripts are correlated with disease progression, said method comprising steps:

(a) detecting separately a level of total RNA and a level of processive viral transcripts;

(b) determining a proportion of total RNA and processive viral transcripts of step (a); and (c) assessing the degree of processivity using a proportion value determined in step (b);

(d) detecting a change of the proportion of TAR fragments to processive transcripts; and (e) correlating the degree of processivity of step (c) and the change of the proportion of step (d) with the determination of and change in degree of HIV latency, activation and disease progression.

9. The method of claim 8 wherein the change in the proportion is indicative of a transition from latent to active HIV replication or from active to latent HIV replication and is correlated with disease progression.

10. An assay for monitoring HIV transcriptional activity and disease progression comprising determining absolute and relative levels of nonprocessive transcription and processive transcription, expressing said levels as a difference or ratio, and correlating a change in said difference or ratio with disease progression wherein a change in said difference or ratio is correlated with a transition from latency to activation, said method comprising steps:

(a) obtaining HIV infected cells;

(b) extracting RNA from the cells of step (a) for direct detection or for detection by target assay or fixing the cells of step (a) for in situ detection;

(c) preparing cDNA from RNA extracted from the cells obtained in step (b);

(d) amplifying the cDNA with a primer set comprising complementary DNA sequences to generate amplification products from a leader sequence of all viral transcripts and with a primer set comprising complementary DNA sequences to generate amplification from the processive transcripts;

(e) detecting the amplified product of step (d) directly or by hybridizing with a labeled probe having a sequence complementary to TAR;

(f) quantitating the difference and the ratio of amplification products; and (g) correlating said difference or ratio with HIV transcriptional activity.

11. The assay of claim 10 wherein a decreased difference or ratio is correlated with a progression of a HIV disease from latency to activation.

12. The assay of claim 11 wherein the product formed in the step (b) of claim 10 is detected by gel electrophoresis, slide-based or flow cytometric detection systems.

13. The assay of claim 11 wherein the product of step (e) is detected by gel electrophoresis.

14. A probe for detection of nonprocessive HIV transcripts comprising TAR sequence wherein said probe comprises a permutation of a sequence complementary to said nonprocessive HIV transcripts, wherein hybridization of adjacent regions of said probe with opposite terminal regions of the products of nonprocessive transcription results in concatamerization of said products.

* * * * *